(12) United States Patent
Shohat

(10) Patent No.: US 10,987,092 B2
(45) Date of Patent: Apr. 27, 2021

(54) SOFT TISSUE FIXATION DEVICES

(71) Applicant: BIOPROTECT LTD., Kfar Saba (IL)

(72) Inventor: Shaul Shohat, Kfar HaOranim (IL)

(73) Assignee: BIOPROTECT LTD., Tzur Yigal (IL)

( * ) Notice: Subject to any disclaimer, the term of this patent is extended or adjusted under 35 U.S.C. 154(b) by 0 days.

(21) Appl. No.: 15/262,166

(22) Filed: Sep. 12, 2016

(65) Prior Publication Data
US 2017/0065265 A1 Mar. 9, 2017

Related U.S. Application Data

(63) Continuation of application No. 12/531,073, filed as application No. PCT/IL2008/000354 on Mar. 13, 2008, now abandoned.

(60) Provisional application No. 61/006,669, filed on Jan. 25, 2008, provisional application No. 60/918,051, filed on Mar. 15, 2007.

(51) Int. Cl.
*A61F 2/00* (2006.01)
*A61B 17/00* (2006.01)
*A61B 17/22* (2006.01)

(52) U.S. Cl.
CPC .... *A61B 17/00234* (2013.01); *A61B 17/0057* (2013.01); *A61F 2/0045* (2013.01); *A61F 2/0063* (2013.01); *A61B 2017/00004* (2013.01); *A61B 2017/00557* (2013.01); *A61B 2017/00792* (2013.01); *A61B 2017/00796* (2013.01); *A61B 2017/22061* (2013.01); *A61F 2002/0072* (2013.01); *A61F 2210/0004* (2013.01)

(58) Field of Classification Search
CPC ..................... A61B 17/00234; A61B 17/0057
USPC ........................................ 623/23.75
See application file for complete search history.

(56) References Cited

U.S. PATENT DOCUMENTS

| | | | |
|---|---|---|---|
| 2004/0093004 A1* | 5/2004 | Schultz | A61B 17/12022 606/192 |
| 2004/0172048 A1* | 9/2004 | Browning | A61F 2/0063 606/151 |
| 2004/0215054 A1* | 10/2004 | Siegel | A61F 2/004 600/31 |
| 2005/0216042 A1* | 9/2005 | Gertner | A61B 17/0401 606/151 |
| 2008/0065229 A1* | 3/2008 | Adams | A61F 2/0063 623/23.75 |
| 2009/0156891 A1* | 6/2009 | Heys | A61F 2/0045 600/37 |
| 2013/0338761 A1* | 12/2013 | Plowiecki | A61F 2/856 623/1.35 |

* cited by examiner

*Primary Examiner* — Suba Ganesan
*Assistant Examiner* — Aren Patel
(74) *Attorney, Agent, or Firm* — Momentum IP; Marc Van Dyke

(57) ABSTRACT

Remodeling of body tissue using a bioabsorbable implant that maintains or otherwise mechanically assists a more permanent implant or other treatment take, for example, by the treatment causing fibrosis. For example, the apparatus and methods can be used for hernia, organ prolapse and cosmetic purposes, such as breast and face lifts.

20 Claims, 10 Drawing Sheets

SOFT TISSUE FIXATION DEVICES

RELATED APPLICATION

This application is a continuation of U.S. application Ser. No. 12/531,073 which has a 371 date of Sep. 14, 2009 and which is incorporated herein by reference in its entirety. U.S. application Ser. No. 12/531,073 is a national phase entry of PCT/IL08/00354 filed on Mar. 13, 2008 which is incorporated herein by reference in its entirety. PCT/IL08/00354 claims the benefit under 119(e) of U.S. provisional application 60/918,051, filed Mar. 15, 2007 and U.S. provisional application 61/006,669 filed on Jan. 25, 2008.

This application is related to a co-filed PCT application with same applicants, PCT/IL08/00347 and entitled "PROSTHETIC DEVICES AND METHODS FOR USING SAME", filed in the IL receiving office.

The contents of all of the above documents are incorporated by reference as if fully set forth herein.

FIELD AND BACKGROUND OF THE INVENTION

The present invention, in some embodiments thereof, relates to devices and methods for soft tissue manipulation and, more particularly, but not exclusively, to soft tissue fixation.

Typically, implants are attached to soft tissue using anchors or sutures. For example, a bladder neck elevation procedure includes inserting sutures under the bladder neck. In a hernia procedure, a mesh is attached to the fascia, using sutures and the like. In some procedures, a soft tissue is grabbed by a permanent implant, such as a clip.

US Patent Application published on 7 Feb. 2008 under Publication No. 2008-0033471-A1, describes moving tissue away from a radiation danger zone using an implantable inserted element.

SUMMARY OF THE INVENTION

A broad aspect of some embodiments of the invention relates to anchoring implants and/or otherwise manipulating and/or remodeling soft tissue, using implantable, bio-absorbable implants, optionally in conjunction with permanent implants.

There is provided in accordance with an exemplary embodiment of the invention, a method of tissue manipulation, comprising:

(a) inserting in the body an expandable bioabsorbable element in mechanical association with a soft tissue;

(b) treating said soft tissue to cause remodeling thereof, with mechanical assistance of said bioabsorbable element, said remodeling to last after said bioabsorbable element dissipates.

In an exemplary embodiment of the invention, said bioabsorbable elements is configured, at least on most of its surface to not cause a fibrosis adhesion to tissue. Optionally, substantially all of said element is configured to not causes a fibrosis reaction.

In an exemplary embodiment of the invention, at least part of said element is configured for causing a tissue adhesion reaction.

In an exemplary embodiment of the invention, said mechanical assistance comprises forming a working volume in or near said soft tissue. Optionally or alternatively, mechanical assistance comprises supporting said soft tissue.

In an exemplary embodiment of the invention, said treatment comprises treatment using an implant and wherein mechanical assistance comprises causing an implant to engage said soft tissue. Optionally, said element is configured to bioabsorb after a time when said implant is expected to adhere to said soft tissue.

In an exemplary embodiment of the invention, said implant is permanent.

In an exemplary embodiment of the invention, mechanical assistance comprises urging said implant against said soft tissue. Optionally or alternatively, mechanical assistance comprises positioning said implant relative to said soft tissue. Optionally or alternatively, mechanical assistance comprises pulling said implant against said soft tissue. Optionally or alternatively, mechanical assistance comprises maintaining a shape of said implant by said bioabsorbable element. Optionally or alternatively, mechanical assistance comprises sandwiching said implant between two bioabsorbable elements.

In an exemplary embodiment of the invention, said implant includes a plurality of tissue engaging elements.

In an exemplary embodiment of the invention, said implant is configured for causing tissue ingrowth.

In an exemplary embodiment of the invention, said element is non-planar.

In an exemplary embodiment of the invention, said element is inflatable. Optionally, the method comprises modifying an inflation of said element after insertion thereof.

In an exemplary embodiment of the invention, said element is deformable. Optionally, said element is pre-filled with a more fluid filling than an outer shell thereof.

In an exemplary embodiment of the invention, treating comprises reinforcing a weakness in a tissue wall. Optionally, said implant is a reinforcing element and wherein said bioabsorbable element is placed on an opposite side of said weakness from said reinforcing element.

In an exemplary embodiment of the invention, said implant is a reinforcing element and wherein said bioabsorbable element is placed on a same side of said weakness as said reinforcing element. Optionally, the method comprises placing a second bioabsorbable element opposite said weakening, for hernia treatment.

In an exemplary embodiment of the invention, said implant is a reinforcing element and wherein said bioabsorbable element comprises two elements, one on either side of said reinforcing element. Optionally, a first bioabsorbable element is placed inside a peritoneum and a second bioabsorbable element is placed in side an inguinal canal and said reinforcement element covers a hernia neck.

In an exemplary embodiment of the invention, said implant comprises two meshes, one positioned on either side of said weakness.

In an exemplary embodiment of the invention, said hole is selected from inguinal hernia, linea alba hernia, femoral hernia and ventral hernia. Optionally, said bioabsorbable element lies in an inguinal canal and causes sealing of a back face of the canal.

In an exemplary embodiment of the invention, treating comprises tightening tissue. Optionally, said tissue comprises subcutaneous tissue. Optionally or alternatively, said tissue tightening comprises lifting sagging tissue. Optionally, said lifted tissue comprises a breast.

In an exemplary embodiment of the invention, lifting comprises:

(a) inserting a device including said biodegradable element between skin and a breast fascia;

(b) engaging said breast fascia with a plurality of tissue engaging elements of said device;

(c) lifting the breast; and (d) engaging a chest tissue with a second plurality of tissue engaging elements of said device. Optionally, the method comprises supporting said breast from a bottom thereof, using a biodegradable element.

In an exemplary embodiment of the invention, said element urges a plurality of facing tissue engaging elements against tissue. Optionally, urging comprises first urging a first set of said tissue engaging elements, then shortening the tissue then urging a second set of said tissue engaging elements. Optionally, said tissue engaging elements are mounted on a plurality of supports and comprising separately moving each of said supports to achieve different foldings of tissue at different locations associated with different supports.

In an exemplary embodiment of the invention, the method comprises inserting a second biodegradable element to support said tissue.

In an exemplary embodiment of the invention, treating comprises supporting an organ. Optionally, said organ comprises a pelvic organ, selected from bladder, uterus, rectum and vagina. Optionally, when the method is used for vaginal prolapse, the method comprises:

(a) separating vaginal tissue from another tissue using said bioabsorbable element;

(b) positioning a reinforcing element between the vaginal tissue and other tissue; and (c) maintaining said reinforcing element in place using a bioabsorbabale expandable element.

In an exemplary embodiment of the invention, said organ comprises a urethra.

In an exemplary embodiment of the invention, supporting comprises supporting a support implant on either side of where said support implant supports said organ.

In an exemplary embodiment of the invention, supporting comprises peripheral support of a support implant.

In an exemplary embodiment of the invention, supporting comprises expanding a peripherally placed bioabsorbable element that is peripheral to a reinforcement element.

In an exemplary embodiment of the invention, treating comprises narrowing a passageway by causing fibrosis adjacent a wall of the passageway, such that said wall extends into the passageway. Optionally, said passageway is selected from a group consisting of a gastro-esophageal junction, a ureteral orifice, a urethra, a bladder neck and an anus.

There is provided in accordance with an exemplary embodiment of the invention, a method of tissue remodeling, comprising:

(a) inserting a device with a plurality of facing tissue engagement elements mounted thereon, between two tissue layers;

(b) causing a first set of said tissue engagement elements to engage a tissue layer;

(c) moving said device while folding said tissue layer; and (d) causing a second set of said tissue engagement elements to engage said tissue layer in a folded form. Optionally, the method comprises leaving said device in said location, to bioabsorb. Optionally or alternatively, the method comprises urging said barbs against said later using an expandable element.

There is provided in accordance with an exemplary embodiment of the invention, a method of tissue remodeling, comprising:

(a) inserting an expandable device against a passageway of a body duct, such that said device causes at least a portion of a layer of said duct to extend into said passageway; and (b) allowing said device to form fibrosis. Optionally, said device is bioabsorbable.

There is provided in accordance with an exemplary embodiment of the invention, a prosthesis, comprising:

(a) a permanent implant adapted to cause a soft tissue reaction of adhesion; and (b) an expandable bioabsorbable implant mechanically coupled to said permanent implant.

In an exemplary embodiment of the invention, said bioabsorbable implant has a consistency similar to that of soft tissue.

In an exemplary embodiment of the invention, said bioabsorbable implant is configured to dissipate after said implant is adhered to soft tissue by said reaction.

In an exemplary embodiment of the invention, said permanent implant is resilient.

In an exemplary embodiment of the invention, said permanent implant is pliable.

In an exemplary embodiment of the invention, said permanent implant is planar.

In an exemplary embodiment of the invention, said permanent implant comprises a reinforcement element.

In an exemplary embodiment of the invention, said permanent implant comprises a mesh.

In an exemplary embodiment of the invention, said permanent implant comprises a plurality of elongate elements, each having at one facing tissue engaging elements at either end thereof.

In an exemplary embodiment of the invention, said permanent implant encourages tissue ingrowth thereto.

In an exemplary embodiment of the invention, said permanent implant comprises a plurality of tissue engaging barbs.

In an exemplary embodiment of the invention, the prosthesis comprises a pharmaceutical eluting portion.

In an exemplary embodiment of the invention, said bioabsorbable implant is configured to avoid tissue adhesion.

In an exemplary embodiment of the invention, said bioabsorbable implant is inflatable. Optionally, said bioabsorbable implant is packaged with an inflation element. Optionally or alternatively, the prosthesis comprises a delivery tube with an inflation lumen. Optionally or alternatively, the prosthesis comprises a delivery tube with two inflation lumens.

In an exemplary embodiment of the invention, said bioabsorbable implant is deformable. Optionally, said bioabsorbable implant comprises a shell and a more fluid interior and is pre-sealed.

In an exemplary embodiment of the invention, said bioabsorbable implant is packaged with at least one delivery tube having a diameter smaller than a smallest dimension of said bioabsorbable implant.

In an exemplary embodiment of the invention, said mechanical coupling comprises a flexible cord.

In an exemplary embodiment of the invention, said mechanical coupling comprises an inflation lumen for said bioabsorbable implant.

In an exemplary embodiment of the invention, said mechanical coupling comprises a mounting of said bioabsorbable implant on said permanent implant.

In an exemplary embodiment of the invention, said bioabsorbable implant is peripherally located with respect to said implant. Optionally, the prosthesis comprises a second bioabsorbable implant.

In an exemplary embodiment of the invention, said bioabsorbable implant comprises two bioabsorbable implants, one on either side of said permanent implant. Optionally, said permanent implant is sandwiched between said two bioabsorbable implants. Optionally or alternatively, said bioabsorbable implant comprises two bioabsorbable implants, one on either end of said permanent implant. Optionally, the prosthesis comprises at least one pull wire adapted to tighten said permanent implant.

In an exemplary embodiment of the invention, said biodegradable implant is an annular balloon and wherein said permanent element is a flat element surrounded by said annular balloon. Optionally, the prosthesis comprises a second annular biodegradable implant surrounding said annular balloon.

In an exemplary embodiment of the invention, said biodegradable implant is configured to shield a side of said implant from tissue.

In an exemplary embodiment of the invention, said biodegradable implant is a balloon surrounded by said permanent implant on at least one side thereof. Optionally, said biodegradable implant is a balloon surrounded by said permanent implant on at least two sides thereof. Optionally or alternatively, said prosthesis is flat. Optionally or alternatively, said prosthesis is sized for an inguinal canal.

In an exemplary embodiment of the invention, the prosthesis comprises a delivery tube within which said prosthesis is enclosed.

There is provided in accordance with an exemplary embodiment of the invention, a prosthesis, comprising:

(a) a bioabsorbable backing expandable expanding element;

(b) a bioabsorbable front, comprising a plurality of facing tissue engaging elements; and (c) a detachable delivery element. Optionally, the prosthesis comprises a mesh mounted on said front.

There is provided in accordance with an exemplary embodiment of the invention, a prosthesis, comprising:

(a) a bioabsorbable mesh in a generally tubular or sealed tubular form, having a distal end and a proximal end; and (b) a puller attached to said distal end, wherein said mesh is configured to radially expand when said puller is retracted relative to said proximal end.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1A:
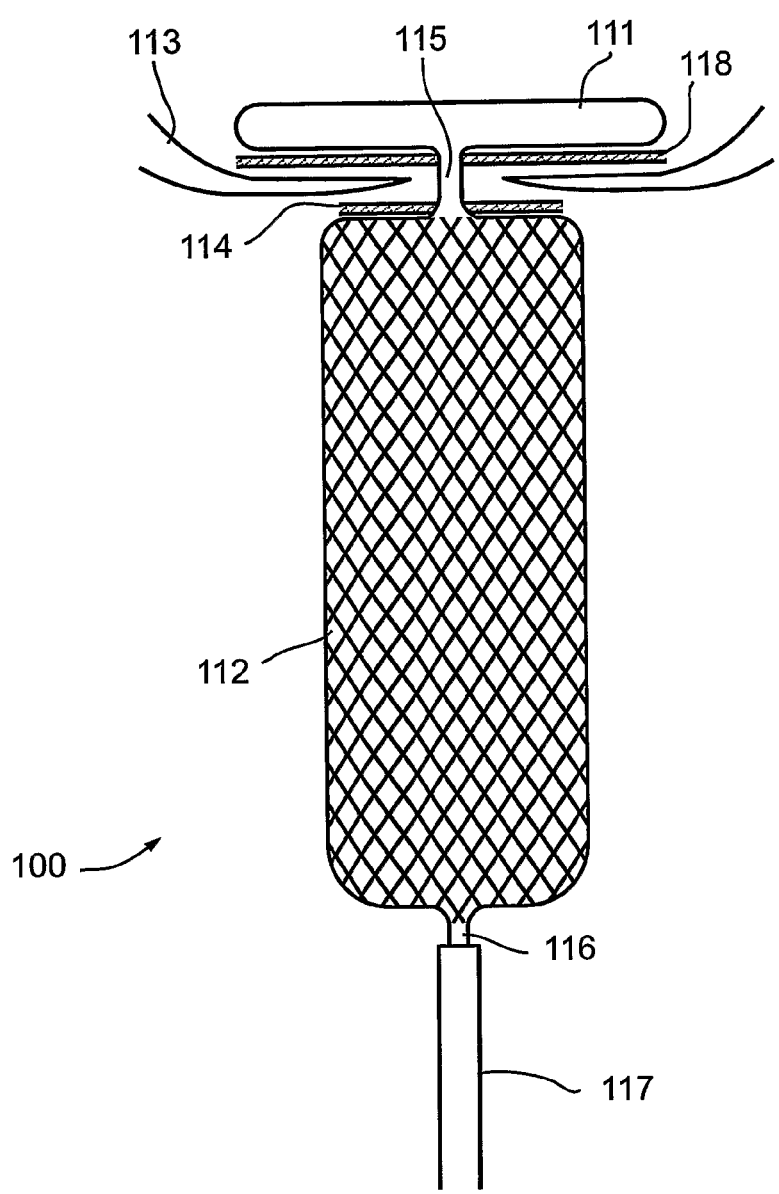
FIG. 1A is a schematic showing of a hernia repair, in accordance with an exemplary embodiment of the invention.

The present invention, in some embodiments thereof, relates to anchoring implants and/or otherwise manipulating soft tissue, especially for remodelling, using implantable, bio-absorbable implants.

Overview

In an exemplary embodiment of the invention, a bioabsorbable implant (or implant portion) is used to manipulate tissue while a non-absorbing, later absorbing or other treatment causes tissue setting in a desired configuration the bioabsorbable implant may be at or near the site of the treatment. In an exemplary embodiment of the invention, this methodology is used for remodeling of soft tissue.

In an exemplary embodiment of the invention, a non-absorbing or slower absorbing implant portion is used to cause fibrosis. Fibrosis may be useful, for example, to attach an implant to tissue (e.g., hole closing or reinforcement) or for filling a volume (e.g., anchoring and/or applying pressure against a tissue). In an exemplary embodiment of the invention, fibrosis formed on a bioabsorbable element tends to not cause permanent adhesions, which property is used in some embodiments of the invention. In an exemplary embodiment of the invention, no permanent fibrosis is formed on the bioabsorbable element. In an exemplary embodiment of the invention, it is desirable that no extra fibrosis be formed in certain parts of the body (e.g., near skin), as such fibrosis may be unsightly and/or uncomfortable, even if the fibrosis does not cause adhesion between separate tissues. As used herein, tissue adhesion can include several types of attachment, for example, fibrosis caused attachment, ingrowth, and/or incorporation in tissue (e.g., by migration). In some embodiments, the fibrosis is useful in and of itself as it changes tissue property (e.g., stiffening a wall weakness). In some embodiments, when a reinforcing element is attached to tissue, the combined tissue/reinforcement element has useful properties, such as resistance to prolapse.

It is a particular feature of some embodiments of the invention, that the bio-absorbable portion of the implant is designed to disappear after it is not needed, for example, after 1-3 days, 1-3 weeks, 1-3 months or intermediate or greater periods. The desired duration may depend, for example, on the tissues involved and/or the functionality of the bio-absorbable implant. In some embodiments, an implant comprises a disappearing portion and a non-disappearing portion. In an exemplary embodiment of the invention, the time is selected according to a setting or semi setting of a desired remodeling effect and/or a desired adhesion effect of an implant.

In an exemplary embodiment of the invention, a manipulation implant comprises an inflatable balloon and/or a deformable elastic element. As used herein, a manipulation implant may form a portion of and/or be mechanically coupled to a non-absorbable implant device.

In an exemplary embodiment of the invention, the manipulation implant is configured to not adhere to tissue, for example, by suitable selection of surface texture, coating and/or eluting pharmaceuticals. Optionally or alternatively, the bioabsorbable implant or portions thereof are selected to not have a soft tissue reaction, such as fibrosis and/or inflammation. Alternatively, the tissue adheres to the implant but the implant is then bioabsorbed (or otherwise dissipated, for example, by breaking down mechanically into a powder).

In an exemplary embodiment of the invention, a manipulation implant is used to urge another implant, for example, a hole closure implant or a reinforcing implant against soft tissue. In an exemplary embodiment of the invention, the pressure applied is of a duration sufficient to encourage mechanical engagement of the tissue by the implant. Optionally or alternatively, the duration is sufficient to allow tissue adhesion between the implant and the tissue, for example, via fibrosis.

In an exemplary embodiment of the invention, a manipulation implant is used as an anchor, which is attached by tension to the another implant. For example, in tissue with an opening, an implant larger than the opening on one side of the opening, can serve as an anchor for an implant on the other side of the opening.

In an exemplary embodiment of the invention, a pair of manipulation implants is used to pinch soft tissue, and optionally an implant, between them. For example, a manipulation implant may be placed on either side of an opening with a connector coupling the two implants.

In an exemplary embodiment of the invention, a manipulation implant is used to spread out, position and/or maintain a position of another implant in soft tissue. For example, in a fascia tissue with an aperture, a round manipulation implant or an implant with a projection will tend to rest at the aperture, thereby being able to maintain or position a mesh at the aperture.

In an exemplary embodiment of the invention, a manipulation implant is used to move tissue, for example, temporarily or permanently, for example until tissue sets in a new position.

In an exemplary embodiment of the invention, a manipulation implant is used to prevent tissue adhesion to another implant, for example, until after inflammation processes are completed in an area being treated.

In an exemplary embodiment of the invention, a manipulation implant is used to maintain a shape and/or function of another implant, until that another implant sets to tissue.

In an exemplary embodiment of the invention, a manipulation implant is used to cause tissue separation and/or dissection, for example, when treating plevic prolapse.

In some embodiments, multiple functions are provided by a same bioabsorbable element and/or by a plurality of bioabsorbable elements. Optionally or alternatively, different bioabsorbable elements perform different functions, such as space forming and stabilization.

In an exemplary embodiment of the invention, there are provided kits including one or more manipulation implants and, optionally, expansion and/or delivery systems therefore. Optionally or alternatively, one or more implants to be used with the manipulating implants are provided as well.

In an exemplary embodiment of the invention, a manipulation implant is provided attached to another implant, for example, directly attached or via a flexible element.

In an exemplary embodiment of the invention, a manipulation implant is used as a permanent (e.g., after adhesion) or temporary plug.

In an exemplary embodiment of the invention, a manipulation implant is used for closing a hole, for example, treating a hernia, for example, by one or more of holding a mesh in place, positioning a mesh, blocking a canal or potential opening, preventing adhesion, moving aside tissue and/or serving as a tension-type anchor. Optionally, two manipulation implants are provided, one on either side of the hole. Optionally or alternatively, two meshes are provided, one on either side of the hole.

In an exemplary embodiment of the invention, a manipulation implant is used for modifying tissue properties, for example, stiffening a sphincter. For example, one or more manipulation implants are used to position and/or adhere a mesh to an outside of a sphincter. Optionally or alternatively, the manipulation implant is used to apply pressure to the sphincter.

In an exemplary embodiment of the invention, a manipulation implant is used for organ support, for example, for mid-urethral support and/or prolapsed prevention. In an exemplary embodiment of the invention, the manipulation implant is used to temporarily anchor a support element, such as a mesh or a hammock, until the element adheres to tissue.

In an exemplary embodiment of the invention, a manipulation implant is used to extend a permanent implant in three dimensions so that a space filling effect of fibrosis is supported. This may be useful, for example, for applying pressure against a sphincter and/or for forming a tissue protrusions (e.g., as a new valve).

In an exemplary embodiment of the invention, a manipulation implant is used for cosmetic surgery. In one example, a plurality of tissue tightening elements is pushed against tissue using a bioabsorbable balloon. In another example, a breast is lifted using a manipulating implant below it. Optionally, a tissue shortening implant is located above the breast, using another manipulation implant. Optionally or alternatively, the breast is attached in position using sutures or other means known in the art.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

Hernia Repair

FIG. 1A is a schematic showing of a hernia repair, in accordance with an exemplary embodiment of the invention.

In an exemplary embodiment of the invention, a hernia repair device 100 includes one or more expanding elements 111 and 112 and one or more meshes 114 and 118. In general, the mesh is positioned, maintained in location and/or urged against a herniated location (hernia neck) 113 by the expanding element(s). Several variations will be described below. For brevity, elements 111 and 112 will be referred to as balloons, as they may be in some embodiments.

Figure 1B:
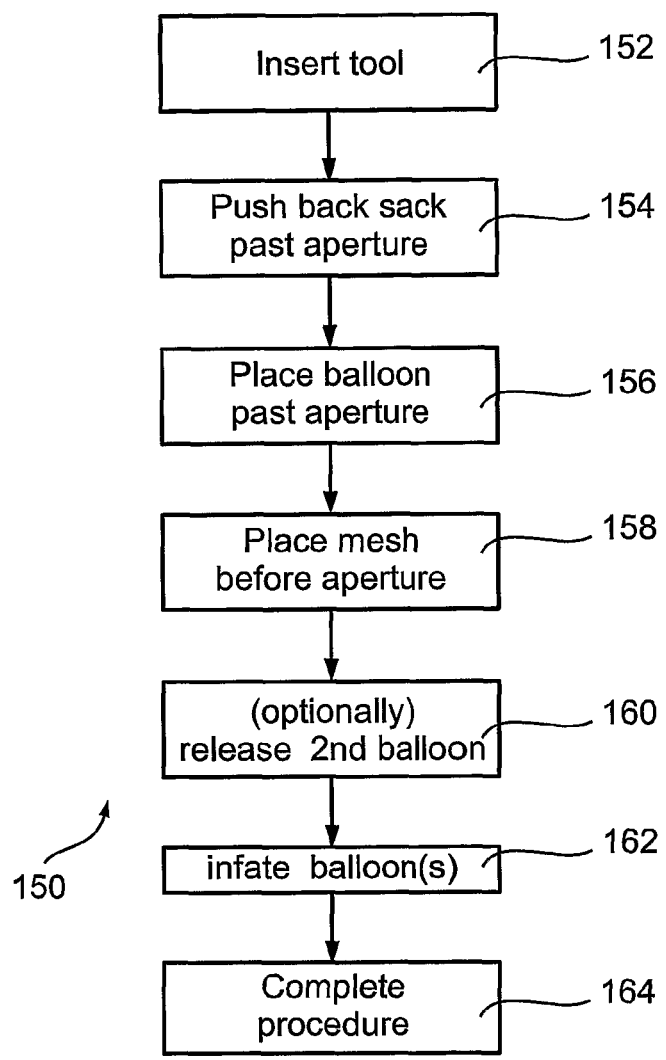
FIG. 1B is a flowchart of a method of hernia repair, in accordance with an exemplary embodiment of the invention.

FIG. 1B is a flowchart of a method 150 of hernia repair, in accordance with an exemplary embodiment of the invention.

At 152, a delivery tool (see FIG. 1C) is inserted into the body, for example, via a small incision or puncture in the inguinal area.

At 154, a hernia sack (if any) is optionally pushed back past hernia neck 113. In case of direct type hernia, the hernia sack is optionally dissected from the elements of the sperm cord, which lies in the inguinal canal and the sack's content is pushed back into the abdominal cavity without opening the sack. The sack is then optionally inverted through the hernia sack neck into the properitoneal space. In the case of indirect hernia, the hernia sack is optionally opened in the inguinal or scrotal region, for example percutaneously, or using a small incision.

At 156, a distal balloon (111) is placed past hernia neck 113. In the case of an indirect hernia, the balloon is optionally placed into the peritoneal cavity and optionally within the sack and will be inflated there.

At 158, a mesh 114 is placed outside the hernia neck 113. In some embodiments, a mesh 118 is placed on an inside of the hernia neck instead of or in addition to mesh 114.

At 160, a proximal balloon (112) is placed outside the hernia neck. In indirect hernia, balloon 112 optionally sits in and plugs the inguinal canal. Optionally, a mesh covering on balloon 112, or on part thereof, is used to adhere to a back side of the inguinal canal (e.g., towards a peritoneum) and seal/prevent other potential direct and/or indirect hernia. Optionally, the mesh serves to fix balloon 112 inside the canal. Optionally, a side of balloon 112 contacting the sperm cord (e.g., a front side, facing the fascia and/or skin) is not covered with a mesh, to avoid adhesions. Optionally, after the procedure is completed and the balloon dissipates, fibrosis formed on the mesh is sufficient to block the openings and/or the canal itself. Optionally, balloon 112 has a square or round cross-section.

At 162, one or both balloons are inflated. Optionally, the distal balloon (111) is inflated first, possibly before positioning the mesh. Alternatively, the inflation is simultaneous, optionally for example, there being a shared lumen 115 connecting the two balloons. As noted below, one or both of expanding implants 111 and 112 need not be balloons.

Alternatively to a lumen 115, another connector is used, for example, a cord, for example and elastic cord. Optionally or alternatively, two or more o the meshes and/or balloons are provided as separate elements. Optionally, a cord extending from the innermost element, e.g., balloon 111, serves as a guide wire along which one or more of the other elements is guided into place (e.g., a mesh and/or balloon riding the cord on a slot or hole in the mesh)

At 164, the procedure is completed. After a while, the mesh(es) adhere to the tissue, for example, via a fibrosis reaction and the balloons dissipate, reducing the amount of foreign material n the body. Optionally, the mesh fibrosis reaction is strong enough so that the fibrosis remains even if the mesh itself also dissipates. Optionally, the balloons may be manipulated after the procedure is completed, for example, being inflated or deflated, for example, using a syringe with a needle. This may assist in ameliorating tissue interaction effects, pain and/or assisting in migration prevention.

In an exemplary embodiment of the invention, the shape and size of the inflatable balloons is so chosen to be larger than hernia neck 113 of the hernia sack. In the embodiment shown, mesh 114 is at least partially situated between the two balloons. In some embodiments, the mesh is attached to some or the entire surface of one or both of the balloons; to some or all of the opposing surfaces of the two balloons and/or be attached to a connecting means 115 (e.g., a cord or an inflation lumen) that connects the two balloons.

In an exemplary embodiment of the invention, the connecting means passes through a small opening in the mesh. In such case, the mesh may not be attached to any surface of the balloon but will remain in proximity to each of them when the balloons are inflated. The connecting means may be used to inflate both balloons through a common inflation port 116, or each balloon may be provided with a separate inflation port. In an exemplary embodiment of the invention, the inflation port is releasable attached to an inflation tube or catheter 117.

In an exemplary embodiment of the invention, balloon 111 serves to prevent adhesion of body organs to mesh 118 and/or mesh 114, by acting as a physical separation. Optionally or alternatively, such separation reduces post-surgical pain, possibly by acting as a physical separation and/or by providing mechanical decoupling (e.g., if the balloon is soft and not hard). Optionally or alternatively, balloon 111 and/or balloon 112 serve to anchor the mesh in place. Optionally or alternatively, the balloons serve to urge the mesh against fascia tissue and encourage adhesions and/or ensure fibrosis is continuous between the fascia and the mesh. Optionally or alternatively, the balloons serve to maintain the shape of the mesh until it sets. Optionally or alternatively, the balloons serve to seal the hernia neck until the mesh can do so. Optionally or alternatively, the balloons serve to position the mesh, for example, by lumen 115 maintaining the mesh in place along the fascia and/or the shape of the balloons encouraging the balloons to remain at hernia neck 113. Optionally or alternatively, the balloons serve to create a working space by moving away tissue, such as bowels. Optionally, the bowels provide the urging force the urges mesh 118 in place.

In the case where two balloons 111 and 112 are used, the balloons optionally sandwich the mesh between them and ensure a minimum desired contact pressure against the fascia of the hernia neck. Optionally or alternatively, such sandwiching prevents migration of the mesh(es) in any direction.

In an exemplary embodiment of the invention, mesh 114 (which is situated on the exterior of the hernia neck) covering it laterally for at least 1 to 2 cm beyond the rim of the hernia neck. In an exemplary embodiment of the invention, the opposing surfaces of the inflatable balloons when inflated are larger than the hernia neck diameter in order to prevent dislodgement of the device from its intended place. It should be noted that having a mesh inside the hernia neck may provide more room for the mesh and allow guaranteeing an overlap of mesh with fascia tissue, optionally to one or two cm, or as otherwise desired, which overlap may not be possible inside an inguinal canal.

Optionally, the proximal balloon (112) situated on the outer side of the hernia neck is flattened on its side to reduce pressure on the cord elements.

Optionally, mesh 114 and/or mesh 118 include one or more extensions (not shown) that are pressed by the inflated balloon(s), especially balloon 112, against the floor of the inguinal canal and may occlude additional direct hernia openings. As shown, a mesh is optionally mounted on balloon 112, on at least one side thereof (in addition to or instead of a front or a back).

As shown balloon 111 is optionally designed to be non-adhesive (e.g., is not covered with a fibrosis encouraging mesh). As noted, balloon 111 optionally hides the meshes from the bowels, to prevent adhesions. In some embodiments, mesh 118, optionally non-degrading, is formed (only) on a proximal face of balloon 111. Alternatively, if a mesh covers the balloon surface in contact with the bowels, the mesh surface facing the bowels is optionally covered with a biodegradable layer made of substances such as but not limited to: PLA, PLGA, polycaprolactone, polydiaxone, collagen, gelatin, albumin, or any combination thereof. Optionally, such layer is configured so that any fibrosis is only formed on the bowels and does not attach the bowels to the mesh, due to the dissipation of the biodegradable layer. Optionally, balloon 111 is flattened on a distal side thereof, to reduce pressure on bowels.

A similar design and deployment method may be used to repair other hernia of the abdominal wall such as linea alba hernias, femoral hernias or postoperative ventral hernias.

A similar method may be used to introduce device 100 laparoscopically. Optionally, device 100 is introduced through a laparoscopic port. In an exemplary method, the distal balloon of device 100 is introduced through the hernia neck into the hernia sack. The proximal balloon is inflated within the peritoneal cavity internally to the hernia neck. Such a method may be very suitable to treat postoperative ventral hernia, especially when such hernia are large and/or the skin adheres to the hernia sack.

As can be seen, in some embodiments and/or cases, the sack is placed back through the hernia neck and in some embodiments it is not. The external hernia sack may be compressed by the balloons or may be allowed to remain. Optionally, balloon 112 when it remains inside the sack and is covered with a mesh, serves to collapse the sack. Optionally or alternatively, a third mesh, proximal to balloon 112 may be used. In an exemplary embodiment of the invention, a mesh covering of balloon 112 contacts the inguinal canal and/or an inside of the sack. In some embodiments, only proximal balloon 112 is used, optionally with a mesh covering (e.g., with or without mesh 114), to block the inguinal canal. In general, it is noted that in some embodiments a mesh and/or balloon are places past the peritoneum and in some embodiments not. Similarly, in some embodiments a mesh and/or balloon are placed past a hernia neck and in some embodiments not.

In some embodiments a deforming element other than a balloon is used. For example, balloon 112 may be replaced by a cylindrical mesh of parallelograms, for example, formed as such or woven or knit. Optionally, a distal end thereof is closed and/or held by a ring. Optionally or alternatively, a proximal end has a rim. In some cases, the mesh is in the form of a sock or otherwise generally cylindrical (e.g., having a length greater than its diameter and being hollow. When axially shortened, such a mesh radially expands, for example, into the form of an ovoid, optionally with a diameter expansion ratio of ×1.5, ×2, ×3 or intermediate or greater ratios. The length may be shortened by a similar amount and is optionally made smaller than the diameter.

Optionally, the mesh is elastic and/or super-elastic and allowed to expand radially when released. Optionally, an inner membrane is provided (similar to a balloon), which is not positively inflated. Optionally or alternatively, the cylindrical mesh is plastically deformed, for example, by pulling a thread connected to a far part of the mesh relative to pushing a pusher (or holding the near end in place) connected to a near side of the mesh. Optionally, a locking location for the thread is provided on a ring mounted on the near end, for example, in the form of a slot in the ring and a matching protrusion in the thread. Other locking mechanisms and/or ratchet like mechanisms may be used. Alternatively a temporary balloon may be inflated inside the mesh and then removed. Various suitable expanding mesh designs are known in the art of stents and may be used. Such an expanding mesh may also be used for bulking uses, for example, for sphincter enhancement, as described below.

In an exemplary embodiment of the invention, device 100 is introduced into place by a deploying means comprising of a tube or sheath, within which the device is folded/compressed and a pusher rod that is used to push out the device at the desired place.

Figure 1C:
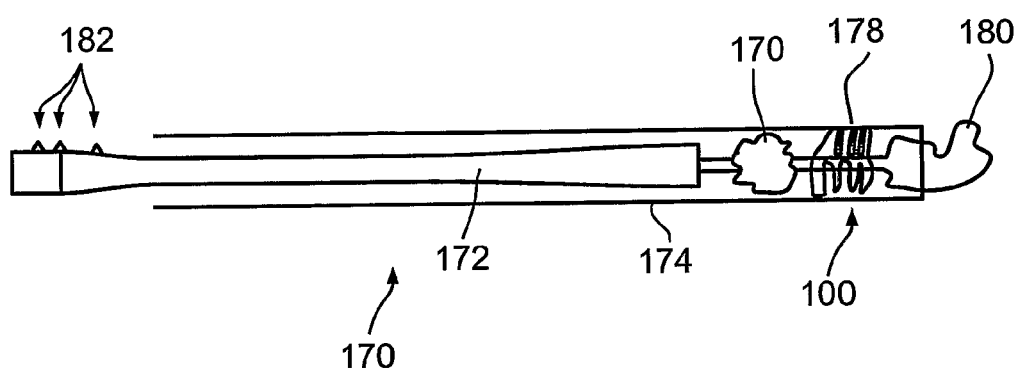
FIG. 1C is a schematic showing of a loaded delivery system, in accordance with an exemplary embodiment of the invention.

FIG. 1C is a schematic showing of a loaded delivery system 170, in accordance with an exemplary embodiment of the invention.

A delivery tube 174, optionally stiff contains a device 100 therein (or another design), including, for example a distal balloon 180, a mesh 178 and a proximal balloon 176. Alternatively, tube 174 may be flexible and/or navigatable. Optionally, before device 100 is pushed out, tube 174 is used to manipulate hernia material.

In exemplary use, a pushing rod 172, which optionally serves as an inflation lumen for device 100 is used to advance device 100 out of tube 174. Optionally, the advancing is in steps, with each step corresponding to a different part of device 100, this may encourage correct placement in the body. Optionally, tube 174, pusher 172 and/or device 100 include radio-opaque markers thereon, to support x-ray visualization of the deployment process. Optionally, a plurality of semi-stops 182 are provided, for example, on pusher 172, so that each stage of device deployment is marked by reaching a stop (e.g., a stop of pusher 172 moving until it abuts a projection on tube 174).

Figure 2:
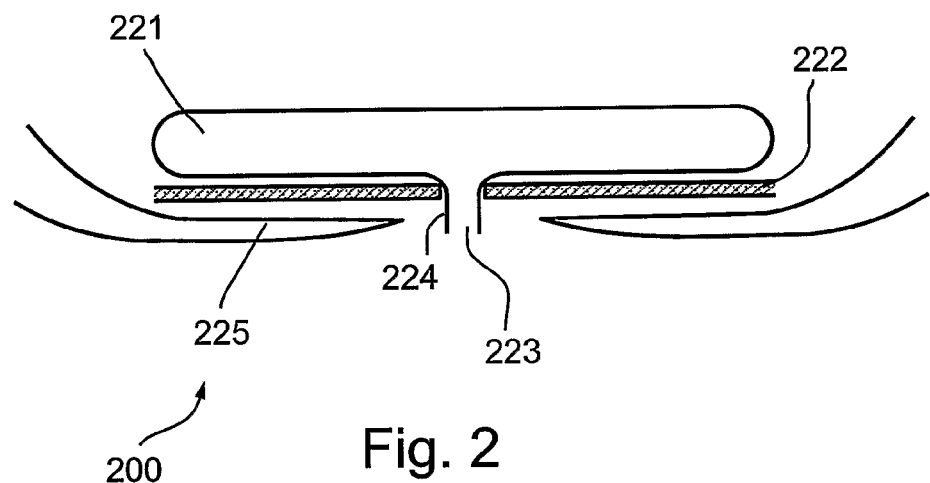
FIG. 2 is a schematic showing of an alternative method of hernia repair, in accordance with an exemplary embodiment of the invention.

FIG. 2 is a schematic showing of an alternative method of hernia repair, in accordance with an exemplary embodiment of the invention. As noted above, various methods may be used, for example, with one or two balloons, one or two meshes, and/or with a balloon and mesh being on opposite sides of eth hernia (e.g., inside or outside) or on a same side. FIG. 2 shows an embodiment of a device 200, where a balloon 221 is on a same (inner) side of a hernia neck 115 as a mesh 222. Depending on the embodiment and/or type of hernia, the mesh may be inside a peritoneum or not.

In an exemplary embodiment of the invention, an element 223 serves for one or more of an inflation lumen, a mesh-balloon coupler, an anchor for maintaining device 200 in the correct location and/or a handle for placement. In an exemplary embodiment of the invention, fascia contact pressure is provided by bowels pressing against balloon 221. Optionally, the balloon is designed, for example, with a cup shape, to prevent slippage of the balloon.

In an alternative embodiment, balloon 221 is provided on an opposite side of the hernia neck from the mesh. In this case, the mesh does not go through the neck do to its being stiff enough to avoid deformation under forces which urge in that direction. Optionally, the balloon keeps the mesh form migrating away form the neck in an opposite or lateral direction.

Cosmetic Tightening

Figure 3A:
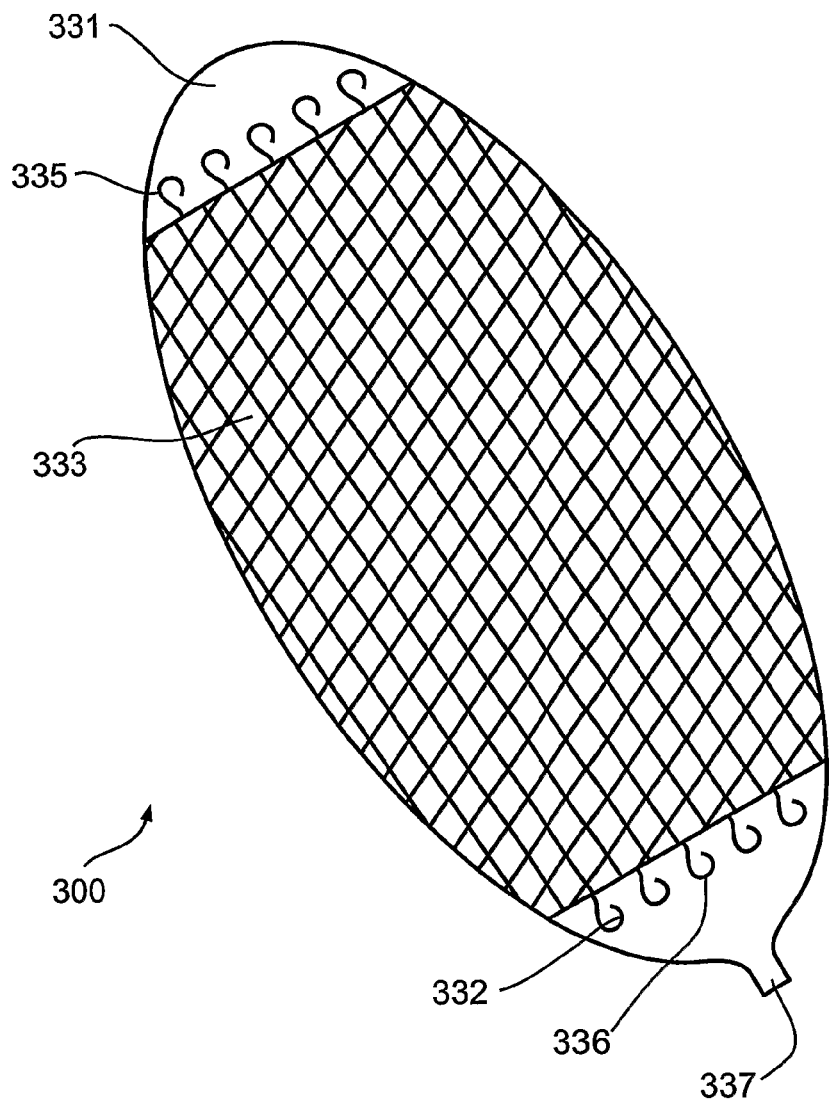
FIGS. 3A and 3B are schematic showings of a device for tissue tightening, such as for a face lift, in accordance with an exemplary embodiment of the invention.
Figure 3B:
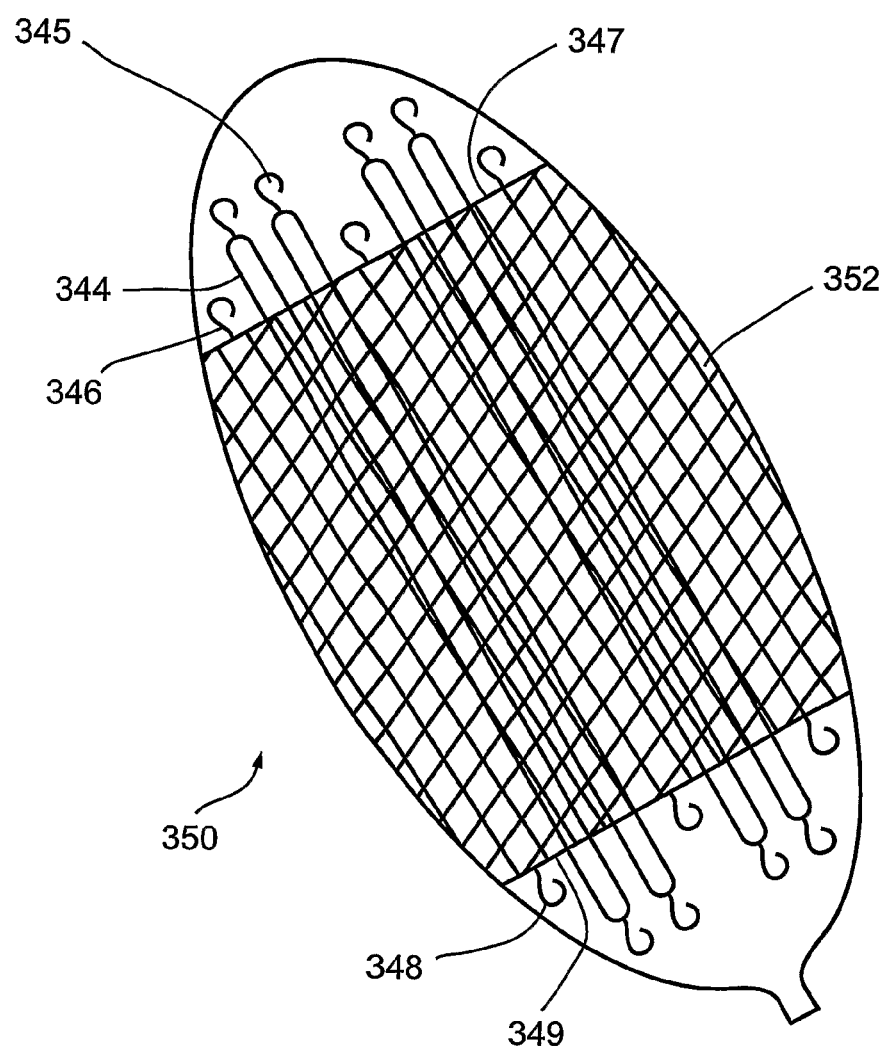

FIGS. 3A and 3B are schematic showings of devices for tissue tightening, such as for a face lift, in accordance with an exemplary embodiment of the invention.

In an exemplary embodiment of the invention, tissue tightening is achieved by causing folding or pleating of the tissue and maintaining the thus manipulated tissue in place until at least some fibrosis sets the tissue. Optionally, a mesh is provided to anchor the tissue in its manipulated condition. In an exemplary embodiment of the invention, a balloon is provided to ensure folding of tissue and/or engaging of tissue by a mesh and/or fibrosis. Optionally, the balloon is removed after the procedure is completed. Optionally or alternatively, the mesh degrades and/or otherwise dissipates after tissue sets in the manipulated condition. In general, in some embodiments, it is envisioned that a mesh is desired to remain permanently in place where forces are large and/or fibrosis may disappear.

In an exemplary embodiment of the invention, the folding of tissue is by using one or more elements that have opposite facing tissue engaging elements, such as barbs or hooks and advancing and retracting the element so that the barbs engage tissue in a folded state. For example, first the device is advanced so that a near barb engages near tissue then the barb is advanced (and tissue folds) and when the device is retracted, the distal barb engages tissue. Optionally, the location of barbs is selected so that a desired fold location is near the barbs.

Referring specifically to FIG. 3A, an expandable means 331, for example, a balloon, with an inflation port 337 is provided. Optionally, the balloon is flattened. A plurality of small barbs or hooks 332 are provided on one or both surfaces of the balloon. These barbs are optionally manufactured of biodegradable material such as but not limited to: PLA, PLGA, polycaprolactone, polydiaxone, or non biodegradable material such as but not limited to: polypropylene, polyester, metal, or any combination thereof. Balloon 331 may be provided on one or both of its surfaces with a mesh like structure 333. The barbs or hooks may be attached to balloon 331 and/or mesh 333. In an exemplary embodiment of the invention, the barbs/hooks face each other and are designed so that when slid relative to tissue in one direction, the tissue slides past and when slid in an opposite direction, the tissue engages the hooks/barbs. Optionally, the barbs/hooks that are situated at a distal side of the device face rearward 335, while these situated at a proximal aspect distally 336.

FIG. 3B shows an alternative embodiment, of a device 350, in which a mesh like structure 352 is provided with one or more ribbons, or filaments of other cross-sectional shape 344, which are provided with small barbs or hooks 345, on a surface opposite the balloon. The ribbons are optionally attached to the mesh and are optionally independently movable along a predetermined path, e.g., each parallel to its main axis. Optionally or alternatively, barbs or hooks 346 may be provided at a distal margin 347 of the mesh on one or both surfaces of the mesh and/or at a proximal side thereof (e.g., one or more barbs 358 may be provided at a proximal margin 359 of the mesh).

In an exemplary embodiment of the invention, the inflatable device may be manufactured of a biodegradable material and may be left in place after deployment of the mesh structure to prevent dislodgement of the mesh during removal of the balloon. Alternatively, the balloon is manufactured of a non-biodegradable material and is optionally removed after deployment of the mesh structure. Optionally, the barbs/hooks are attached only to the mesh structure.

Optionally, the mesh is biodegradable. Alternatively, the mesh is permanent. As noted above, the mesh is optionally provided for ensuring fibrosis (or other setting) of the folded layer in a desired configuration and/or barbs are provided for manipulating the layer to that configuration and/or to maintain it while the tissue sets. Optionally, such elements may be removed and/or dissipate once their functionality is not needed. In some cases, such as for a belly tuck, it may be believed that large forces are expected over time and/or it may be believed that fibrosis may dissipate, so a permanent mesh may be used. Optionally, the barbs are made of a bioabsorbable material.

As described below, a non-balloon expandable structure may be used as well.

In an exemplary use, device (300, 350) is introduced under the skin of the face in the proper direction through a small incision, optionally after local anesthesia. Optionally, the device is introduced between the skin and SMAS layer. Alternatively, the device is inserted below the SMAS layer.

The device is then expanded (e.g., in a direction perpendicular to the skin) under the skin and separates the SMAS layer and/or the overlaying skin from deeper tissue of the face and/or the neck region (or other region being treated). The distal barbs or hooks provided with the inflatable or expandable device will pierce the SMAS layer and the device is retracted pulling the SMAS layer and folding it on itself in the proper direction. The barbs or hooks situated at the proximal side of the device will be fixed to the tissues below the skin at the new location holding the SMAS layer folded in a desired manner. The excess skin is optionally trimmed and the skin sutured in place without tension. In case of incorporation of ribbons 344, provided with barbs, pulling on these ribbons (e.g., each one including a separate pulling thread, not shown, which reaches to outside of the body) individually may permit differential tensioning of different region of the SMAS layer to the desired degree.

If placed below the SMAS, skin-side barbs may be used to engage the SMAS form underneath, rather than form above, as when the device is placed above the SMAS.

In an exemplary embodiment of the invention, the barbs/hooks are provided folded towards the device, so they do not engage tissue. However, inflation of balloon 331 causes the barbs to extend outwards so they can engage tissue. In an exemplary embodiment of the invention, each barb is mounted on a small plate that is parallel to the surface of the balloon. However, when the balloon is uninflated, this surface may be undulated. When the balloon is inflated, the surface of the balloon flattens, optionally causing the barbs to stick out in a pre-defined configuration.

In some implementations, the tensioning elements are provided separate from the balloon, for example, each one mounted on a separate handle and/or with an extension strip or thread. Optionally, the use of separate elements allow better control of the tensioning/folding of each part of the folded tissue.

A similar device may be used to tension loose skin and underlying loose fascia in other areas such as the neck the eyelids and also for tensioning other tissues such as breast for breast lift.

In another example, the lifted tissue carries significant weight. An additional support element is optionally used. For example, in case of breast lift, the device is optionally introduced under the skin from the anterior axillary line or from the sub-mammary crease and passed under the skin above the nipple and directed toward the clavicle and upper side of the torso. After deployment, the barbs provided at the proximal margin and lower or deeper surface of the device will pierce the fascia covering the mammary tissue. The device is pushed with the engaged breast tissue and covering skin towards the upper side of the torso close to the clavicle and the distal barbs are pressed to penetrate the fascia covering the pectoralis muscle. In that manner the deployed device lifts the breast tissue and the overlying skin and nipple to a desired position.

In an exemplary embodiment of the invention, device 300 or device 350 can be undone (e.g., during the procedure and/or shortly afterwards) by pulling back the device and manually detaching the proximal barbs. Optionally, the balloon is deflated to assist in such detaching.

In case of a large breast or a significantly sagging breast (or other large tissues, such as for gluteoplasty) a biodegradable balloon may be used to push up or otherwise reposition the manipulated tissue, while the mesh sets. For example, for a breast, such a balloon is positioned through the sub-mammary crease bellow the breast and left inflated to support the breast during incorporation of the mesh to prevent its dislodgement. Such an inflatable balloon may have a cup, for example, to support the breast tissue during this period. It should be noted that the two functionalities—fibrosis encouraging mesh for tissue shape setting and bioabsorbable balloon for tissue positioning/support, need not be mechanically connected, but are optionally provided together in a kit, optionally with instructions. In another embodiment, the balloon is attached and/or a non-inflating support is sued, for example, if the device 300 is provided with a sling the lies under the breast. Optionally, two devices 300 are provided, one on each side of the sling.

Tissue Properties Modification and Space Filling

Figure 4:
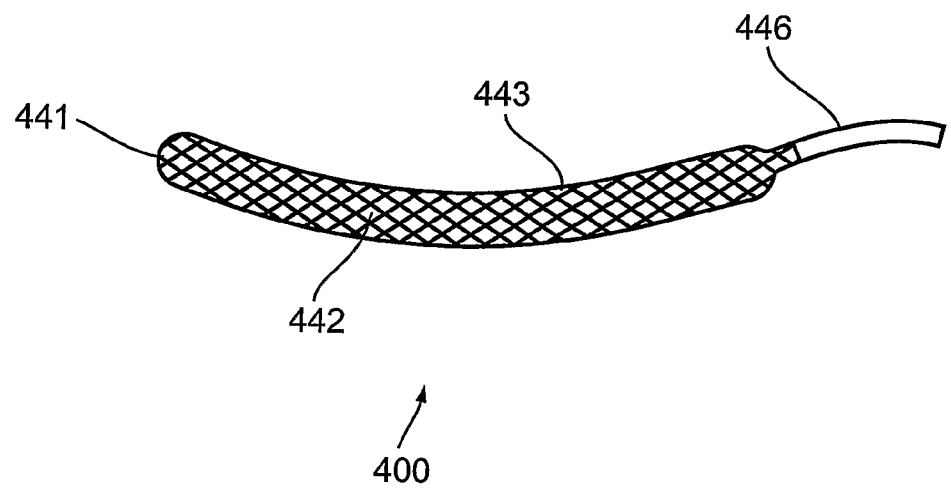
FIG. 4 is a schematic showing of a device for sphincter treatment, in accordance with an exemplary embodiment of the invention.

FIG. 4 is a schematic showing of a device 400 for sphincter treatment, in accordance with an exemplary embodiment of the invention. In general, two types of treatments are envisioned. In a first treatment method, a device 400 provides space filling and is used to constrict a sphincter (or other overly spacious location, such as a potential hernia), by encouraging fibrosis in a volumetric form. Optionally, a plurality of such space fillings are provided, for example, outside the sphincter or inside of it. Optionally, a new valve is defined by providing a plurality of such forms in an annular arrangement, so that an outlying muscle can selectively seal a passageway through a hollow organ, at the created annulus. In a second treatment method, a bioabsorbable balloon, for example, as described with reference to FIG. 1 is used to encourage a mesh or reinforcing fabric or other element, to bond to a tissue, such as the sphincter, with or without first manipulating the sphincter (e.g., folding or radially compressing, at least in part of a diameter thereof, as in the embodiment of FIG. 3). Once bond, the properties of the sphincter and/or other tissue are modified by the adhered element. In some cases, once fibrosis on the tissue is caused, the element may dissipate.

Referring specifically to FIG. 4, device 400, as shown is optionally used for reinforcement of sphincters of hollow organs, for example, for reinforcement of a lower esophageal sphincter and treatment of gastro esophageal reflux.

Device 400 comprises an inflatable biodegradable balloon 441 covered on some, or on all of a surface thereof 442 by a mesh structure 443. Optionally, the shape of device 400 is an elongated shape, for example, a curved cylinder or a section of a cylinder. In an exemplary embodiment of the invention, device 400 is delivered folded within a delivery tube through a gastro scope or along a gastroscope and is optionally introduced between the mucosa and esophageal muscle at the lower end of the esophagus by a pusher. In an exemplary embodiment of the invention, device 400 is inflated by an inflation tube or catheter 446 releasable attached to device 400 and sealed by a sealing mechanism. Several variants are described below. Optionally, this procedure is repeated at multiple points, optionally in an annular form, for example, until a good cooptation of the mucosa at the lower esophageal site is created in a manner that prevent or reduces reflux of gastric content. Optionally, by providing such constrictions at a location of a sphincter muscle, possibly with reduced radial restriction ability, that muscle can now seal the sphincter opening due to the narrowing provided.

Other shapes of device 400 may be provided, for example, a torus or inflatable sleeve provided with mesh on its external and internal surface. Optionally, the use of a more volumetric element supports the formation of a volumetric fibrosis, for example, similar to those provided using bulking agents, albeit, possibly with better control over the shape of such volumetric fibrosis.

A similar procedure may be performed to reinforce other sphincters such as an internal, or external uretral sphincter using a cystoscope, or for reinforcement of the anus. For example, for the uretra, bioabsorbable and/or non-bioabsorbable fibrosis causing elements are optionally implanted in the bladder between the moscosa and the muscle. For example, in the urethra, implants may be provided from within the urethra or form outside the urethra, for example, at the bladder neck.

Tissue and Organ Support

Figure 5:
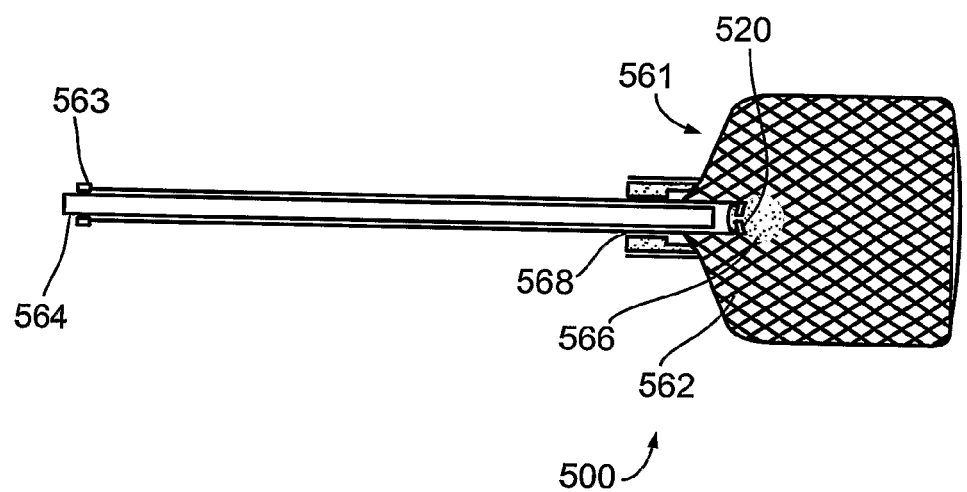
FIG. 5 is a schematic showing of a device for tissue dissection and/or tissue reinforcement, in accordance with an exemplary embodiment of the invention.

FIG. 5 is a schematic showing of a device 500 for tissue dissection and/or tissue reinforcement, in accordance with an exemplary embodiment of the invention. Examples of tissues which may be reinforced include, but are not limited to, abdominal cavity wall, diaphragm, and pelvis. Such weak regions may be represented, but without limitation, by abdominal wall weakness such as hernia, or weakness of the vaginal walls such anterior vaginal wall prolapse, posterior vaginal wall prolapse, uterine or vaginal cuff prolapse, and urinary incontinence by hypermobility of urethra.

Device 500 and/or other devices, with or without a reinforcement element, may be used for other purposes such as separating tissues to prevent damage to some tissue during treatment of adjacent tissues.

Device 500 comprises a flattened expandable, optionally inflatable, optionally bioabsorbable, chamber 561 and a tissue reinforcing structure 562 that is attached to one of both of the flattened surfaces of chamber 561, or incorporated within a wall of chamber 561. An optional inflation port 563 is provided.

In an exemplary embodiment of the invention, a suitable delivery system includes a trocar 564 that is optionally introduced into the inflatable device through the inflating port. Alternatively, a deflated and/or folded device 500 is introduced through a pre-positioned tube.

In an exemplary embodiment of the invention, device 500 is manufactured of a biodegradable biocompatible material as described herein. In an exemplary use, device 500 is introduced to a desired location adjacent weakened tissue, such as but not limited to, between the fascia and skin, or between the fascia and the peritoneum, and inflated under direct vision or another imaging method such as ultrasound, Laparoscopy (visual), CT or MRI. Then, the trocar is removed and chamber 561 is inflated (optionally dissecting the tissue), optionally under continuous monitoring by the imaging means or by direct vision. Alternatively, the device is inflated in place after dissection and separation of tissue by other means.

In an exemplary embodiment of the invention, the tissue reinforcing structure is deployed by the fully inflated device, in its proper place without the need for additional and possibly cumbersome manipulations. In the case of a biodegradable inflatable device, the entire or part of the device may be left deflated in place to prevent dislodgment of the tissue reinforcing means. Alternatively, the device is left inflated and sealed. The decision of to deflate or not, may depend, for example, of danger of dislodgment of the reinforcing structure (e.g., if it does or does not have tissue engaging means such as barbs, hooks or other projections) and/or need to apply pressure.

FIG. 5 shows an exemplary design for selective detachment of lumen 563 and sealing of chamber 561. In an exemplary embodiment of the invention, lumen 563 is coupled to chamber 561 via a neck 568, shown in a cross-sectional view. A plug 566 is held by one or more elements 520, for example, proximally pointing barbs, to a distal end of lumen 563. When lumen 563 is retracted, the plug detaches from lumen 563 and engages the inside of neck 568, sealing chamber 561. It should be noted that sealing requirements may be less stringent as the pressures of inflation may be low, for example, 0-1, or about 0.2 atmospheres above ambient. In an exemplary embodiment of the invention, the pressure is selected so that the balloon is inflated but not stiff.

In an alternative embodiment, lumen 563 is removed by twisting off, the twisting causing a sealing of a distal part of lumen 563, which is optionally provided with a self-adhesive inner lining. Optionally or alternatively, a one way inflation valve (not shown) is provided at neck 586 and lumen 563 is unscrewed from neck 568, to which it is attached using threading. In an exemplary embodiment of the invention, lumen 563 is held in place by friction and can be simply pulled back. Optionally or alternatively, lumen 563 sits in a one way valve, so that when the lumen is pulled out, the valve seals in fluid. Optionally or alternatively, the lumen is soft enough to be tied, for example with a knot being preformed and tightened to seal and/or a new knot made and advanced when needed. Optionally, lumen 563 is formed of a bioabsorbable, non-fibrotic material.

In an exemplary embodiment of the invention, chamber 561 serves to maintain a shape of reinforcement element 562 until it sets in place. Optionally or alternatively, chamber 561 serves to define a working space.

In variants of this and other embodiments, chamber 561 may be on a same side of device 500 as is adhering to tissue and/or on an opposite side, or within device 500.

Figure 6A:
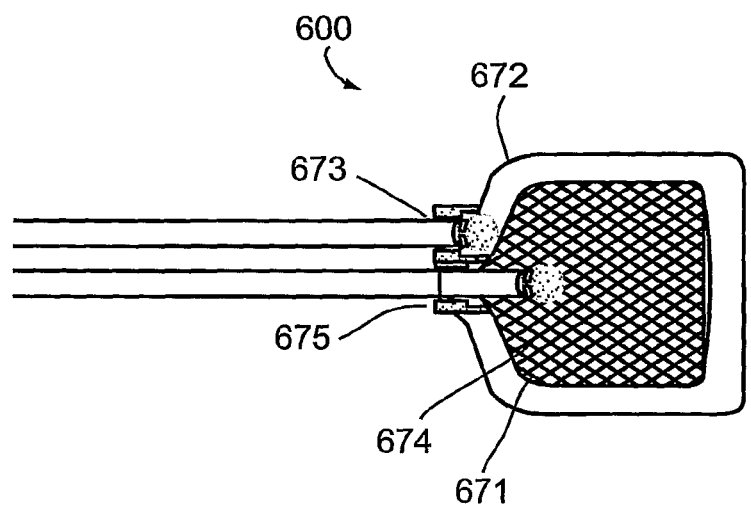
FIGS. 6A and 6B are schematic showings of multi-chamber tissue support devices, in accordance with exemplary embodiments of the invention.
Figure 6B:
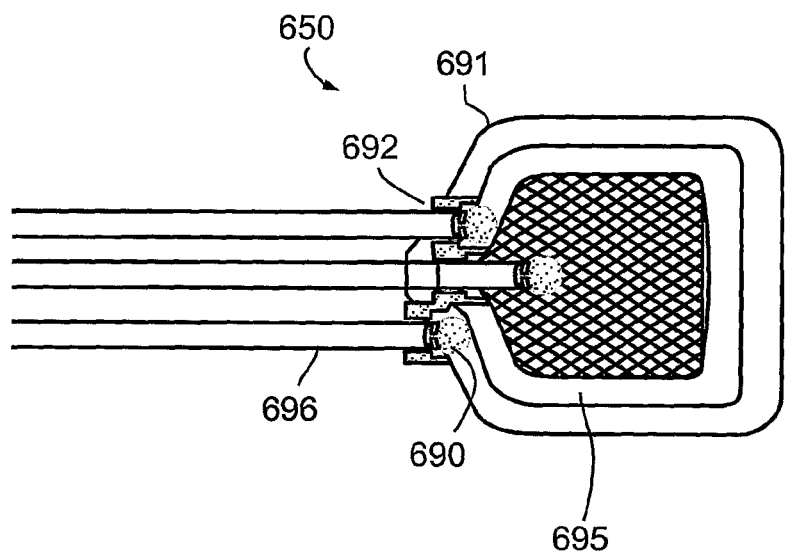

FIGS. 6A and 6B are schematic showings of multi-chamber tissue support devices, in accordance with exemplary embodiments of the invention.

In an exemplary embodiment of the invention, the multiple chambers serve for different functions, for example, one or more of, spacing tissue, positioning, anchoring, maintaining location, maintaining shape of a reinforcement element and/or matching different conditions. For example, FIG. 6A shows an inner chamber and a peripheral chamber. The inner chamber may be deflated before completing the procedure (e.g., being sued for creating a working volume, dissection and/or positioning), while the peripheral chamber is used for maintaining the shape of the reinforcing element and/or anchoring thereof and is left inflated.

The chambers may be on a same side of the reinforcing element or on opposite sides and/or in a same plane as the element.

FIG. 6B shows an embodiment with two peripheral chambers, which are optionally selectively expanded according to the size needed, as determined during a procedure.

Referring specifically to FIG. 6A, an inflatable device 600 comprises a central flattened chamber 671, and at its periphery another chamber is provided 672, surrounding the central chamber. These inflatable chambers are preferentially, manufactured of biocompatible biodegradable material. In an exemplary embodiment of the invention, each chamber is provided with its own inflating port 673, 675. One or more tissue reinforcing structures 674 are attached to one or both flattened surfaces of the device.

In exemplary use, after introduction of the device in its proper place and inflation, the reinforcing structures serve for tissue reinforcement. Optionally, the central chamber is then deflated and only the peripheral chamber is left inflated acting as frame for the mesh structure and/or preventing its displacement after the operation. While the peripheral inflatable chamber is shown as constituting a complete frame, in some embodiments, only a partial frame, for example, covering only 70%, 50%, 30% or intermediate or lesser percentages of the periphery of the device. Optionally or alternatively, two or more separate inflatable chambers may be provided along such perimeter or circumference. As in some other embodiments, the inflatable chambers optionally will biodegrade/bioabsorb in a manner timed to be after the reinforcing element is fixed by fibrosis tissue. Optionally, device 600 is used for abdominal wall hernia.

In case of a vaginal wall prolapse, the following procedure is optionally used. Optionally, the device is used to separate the vaginal wall from a nearby, prolapsing organ. As in a hernia, balloons, meshes, on either side of a fascia (if any) which lies between the organ and the vagina, may be used. In an exemplary embodiment of the invention, the mesh and/or balloon are ring shaped and they act to reinforce the fascia, for example, on a vagina side or on an organ side thereof. The balloon optionally keeps the mesh in place. In an exemplary embodiment of the invention, the use of a mesh and a balloon, allows attachment of the mesh in a manner which is difficult or impossible in open surgery, which would require suturing out from mesh towards fascia. Optionally, the mesh and/or balloon also reposition and/or hold the organ in place.

First, a small incision is performed in the vaginal mucosa and a tunnel is created between the vaginal wall and the adjacent organ—urinary bladder in case of anterior vaginal wall and rectum in case of posterior vaginal wall. The device is provided through a sheath or tube (which may be used to form the tunnel. Optionally, the sheath is provided with a stylet (optionally sharp, alternatively pointed but blunt) for forming the tunnel, and then the stylet removed and the device inserted. Then, device 600 is inflated such that the reinforcing element is deployed between the vaginal wall and the adjacent organ covering the area of weakness in the intervening fascia and/or other tissue. Optionally, the peripheral frame is left inflated and is sealed in this state, preventing displacement of the mesh during the period within which the reinforcing element (e.g., a mesh) is incorporated by fibrosis tissue. Optionally, the mesh and inflatable element and/or a bioabsorbable layer are arranged so that the mesh is incorporated only in the fascia and/or only in the organ and/or in both, as desired. Optionally, the peripheral frame when inflated serves as a splint for the vaginal wall and/or the uterus preventing uteral descent and reducing uterine prolapse that is frequently associated with vaginal wall prolapse. This may reduce the need to perform hysterectomy. It should be noted that if the hernia is small, a ring (or other closed shape, such as a polygon) shaped balloon, may be sufficient for keeping a mesh in place and/or in shape, as the ring will not fit through the hernia neck.

FIG. 6B shows a device 650 with a plurality of concentric inflatable frames 691 and 695 which may be inflated by different ports 692 and 696. This design may be useful when the size of the space to which the mesh should be fixed differs significantly between patients. Optionally, a plug 694 is used to seal ports after use and/or if not used (e.g., before inserting into the body). Optionally, the frames are not concentric, for example, including some overlap and/or each one used to anchor and/or support a different part of the reinforcing element. Optionally, different shapes are used, for example, L shaped, C shaped and U shaped. Optionally or alternatively, different cross-sections are provided for different peripheral balloons, for example, round, square and/or triangle. Optionally or alternatively, different expansion mechanism are used for different ones of the balloons, optionally, one or more of the balloons not being inflated, but being otherwise expandable. Optionally or alternatively, the balloons are on opposite sides of the mesh, optionally with overlapping coverage. Optionally, the frames are on same sides of the reinforcing element. However, they may be on opposite sides, in some embodiments and/or on opposite side of chamber 671 from the reinforcing element.

In an exemplary embodiment of the invention, separate lumens are used for each chamber. Alternatively, a same lumen is shared by multiple chambers. For example, chamber 672 may be inflated by fluid coming from chamber 671. Optionally, a valve is provided, so that when chamber 671 is deflated, chamber 672 remains inflated.

In an exemplary embodiment of the invention, inflation and deflation is using a low pressure source, such as a syringe. Optionally, the fluid pathway includes a safety valve which releases fluid if the device is being over inflated, for example, to prevent tissue damage or mismanipulation.

Figure 7A:
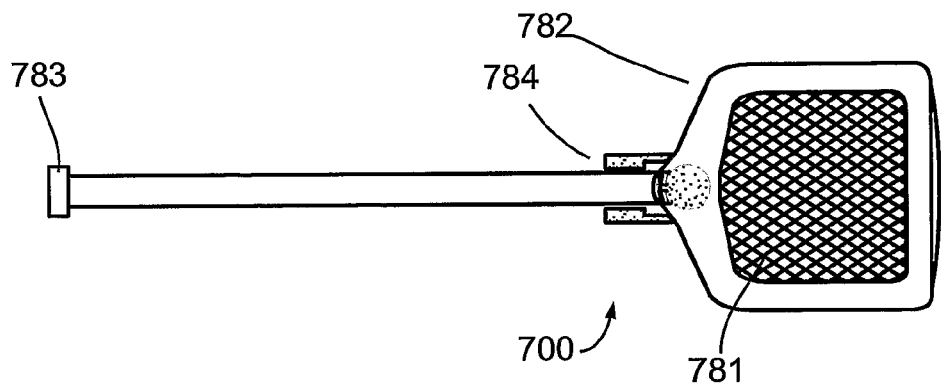
FIGS. 7A-7C are schematic showings of alternative peripheral type tissue and implant support devices, in accordance with exemplary embodiment of the invention.
Figure 7B:
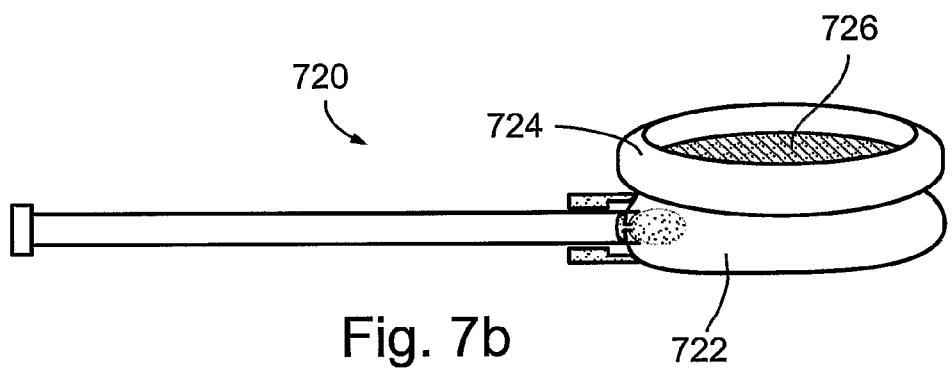
Figure 7C:
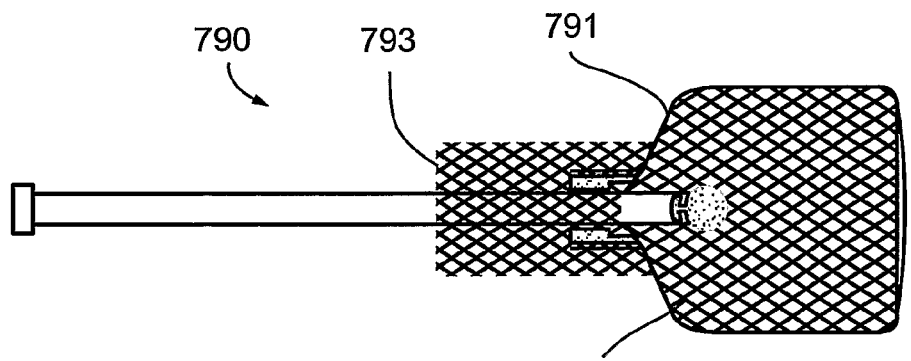

FIGS. 7A-7C are schematic showings of alternative peripheral type tissue and implant support devices, in accordance with exemplary embodiment of the invention.

FIG. 7A shows a device 700 with a tissue reinforcing structure 781, provided with an inflatable chamber 782, only along its perimeter or circumference (possibly excepting extensions of structure 781, for example as described below). This inflatable chamber is provided with an inflation port 783, which may be sealed by a sealing means 784 (e.g., a bioabsorbable plug). The inflatable chamber is optionally made of a biodegradable material. In an exemplary embodiment of the invention, the tissue reinforcing means is a mesh structure that is positioned in place, optionally after proper dissection of tissues and then the inflatable chamber is inflated and sealed and serves as a frame to prevent displacement and/or distortion of the mesh after the operation. As described above, the peripheral inflatable chamber may constitute a complete frame or may be only along part of the perimeter or circumference of the tissue reinforcing means. Additionally, two or more separate inflatable chambers (with shared or not shared lumens) may be provided along such perimeter or circumference.

FIG. 7B shows a device 720 with inflatable frames 724 and 722 on either side of a mesh 726. these chambers may share an inflation lumen or not. In an exemplary embodiment of the invention, these inflation frames serve to prevent dislodgement of the reinforcing means on either side of the weakened region of the abdominal wall or any other cavity wall such as the vaginal wall that is reinforced. In an exemplary embodiment of the invention, device 720 is introduced as a plug through a weakened wall through a discontinuity in the fascia. Then, one of the peripheral rims that serve as a frame is inflated bellow the fascia fixing the device within the weakened wall. Optionally, the second rim may be inflated above the fascia level, preventing dislodgment of the device and spanning the discontinuity in the fascia. Optionally, the inflatable chambers extend laterally beyond the mesh 726, so that fascia or other tissue can be engages and held between the two chambers.

In one embodiment of the invention, two or more chambers are stacked on a same side of mesh 726 and serve to select a degree of protrusion of the rim away from the mesh. The distance can be varied by modifying inflation pressure and/or number and/or selection of chamber inflated (e.g., not all chambers need have the same dimensions).

FIG. 7C shows a device 740 which is optionally used for indirect inguinal hernia repair. Device 740 comprises an inflatable biodegradable balloon/chamber 791, that incorporates in some or all of its wall structure a non-biodegradable material such as a mesh 792. Optionally, a non-biodegradable material such as mesh is provided around a distal side of an inflation port 793. In case of indirect inguinal hernia and especially, in case of inguino-scrotal hernia, the following procedure is optionally used. An incision is performed in the groin revealing the hernia sac. The sac is opened and one of its walls may be opened up to the internal ring of the inguinal canal. The device is introduced through the opening in the sac above the opening of the internal inguinal canal into the peritoneal cavity and chamber 791 inflated. Optionally, care is taken that the inflated device fully covers, from inside, the entire orifice of the internal inguinal ring. Optionally, the surfaces of device 740 facing towards the bowels are covered by biodegradable material, which prevents adhesions and/or may induce coverage of the device by the peritoneum. Optionally, the underlying non-biodegradable mesh structure causes permanent fibrosis which may prevent recurrence of the hernia after the biodegradable material is absorbed. Then, the inflation port is sealed and the distal side of the inflation port (which remains attached to chamber 791) is optionally attached by suturing or other means to the soft tissues in the inguinal canal to prevent dislodgement of the inflated device inside the abdominal cavity. Optionally or alternatively, the additional mesh tissue attached to the device induces fibrosis within the inguinal canal. Such an extension may be provided with other of the embodiments described herein.

Figure 8:
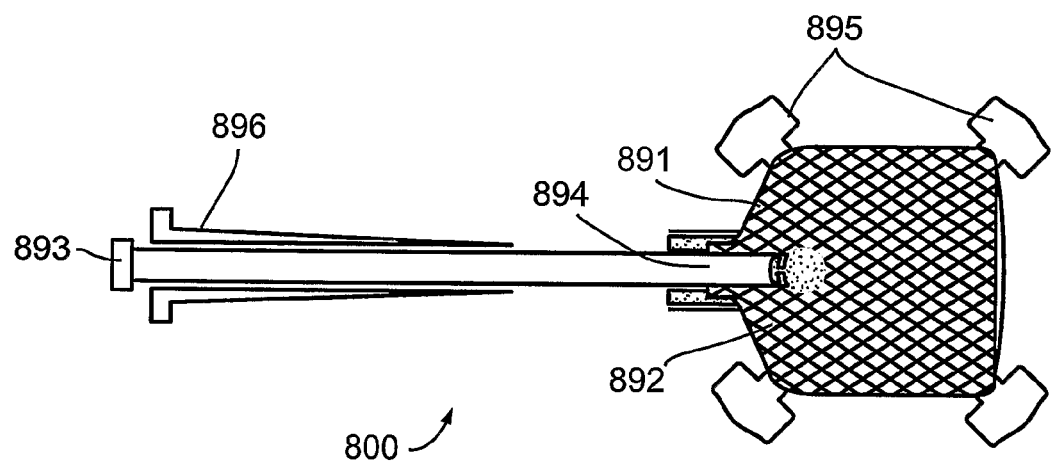
FIG. 8 is a schematic showing of a tissue and implant support device including a plurality of extensions, in accordance with an exemplary embodiment of the invention.

FIG. 8 is a schematic showing of a tissue and implant support device 800 including one or more expanding extensions 895, in accordance with an exemplary embodiment of the invention. In an exemplary embodiment of the invention, extensions 895 are in additional to an expandable chamber 891. Optionally or alternatively, only anchors are provided.

In an exemplary embodiment of the invention, an expandable anchor 895 operates as follows. A tunnel is formed in tissue (or ne exists before, with a certain diameter. An expandable anchor 895 is advanced through the tunnel and inflated to have a larger diameter, optionally in the tunnel. Anchor 895 does not now retract as its diameter is too large to fit through the tunnel diameter. Such an anchor may be loosely coupled to an implant to be anchored, for example as described below, or, for example, as described above in some of the hernia embodiments.

In some cases, the anchors operate without any tunnel being formed, for example, being generally larger than a distance supported between two tissues in normal situations.

The shapes of extensions 895 can be various and are, for example, spherical, elongated and/or start shaped.

Referring specifically to FIG. 8, a chamber/balloon 891 is provided with a tissue reinforcing means, or mesh structure 892 attached or engaging at least some of its surface, an inflation port 893 and a sealing means 894. In addition the balloon is provided with extensions 895, for example in the form of rods, barbs, or projections may be extended laterally during inflation of the balloon.

In use, device 800 is housed into an introducer sheath 896 that may be straight, curved, rigid, semi-rigid or flexible and is optionally sharp at its ends so it can serve to form tunnels in soft tissue. The introducer with the deflated balloon is introduced into its proper place, by advancing the introducer through tissues; the balloon is released and inflated by the inflating means. Since the diameter of the inflated balloon is much larger than the diameter of the channel created within the tissue by the introducer the balloon may serve as an anchor since it will be very difficult to pull it trough the much narrower introducing channel. If a plurality of extensions 895 are provided, each one can anchor separately. Optionally, each of extensions 895 forms its own space. Optionally, a higher pressure is used for inflation than for maintenance, so that balloons are softer during usage than during insertion. Optionally, at least one extension, and optionally two, lie along an axis of introduction (e.g., on distal and proximal sides of mesh 892, along a vector defined by introducer 896 and/or lumen 893.

Urethral Support

Figure 9:
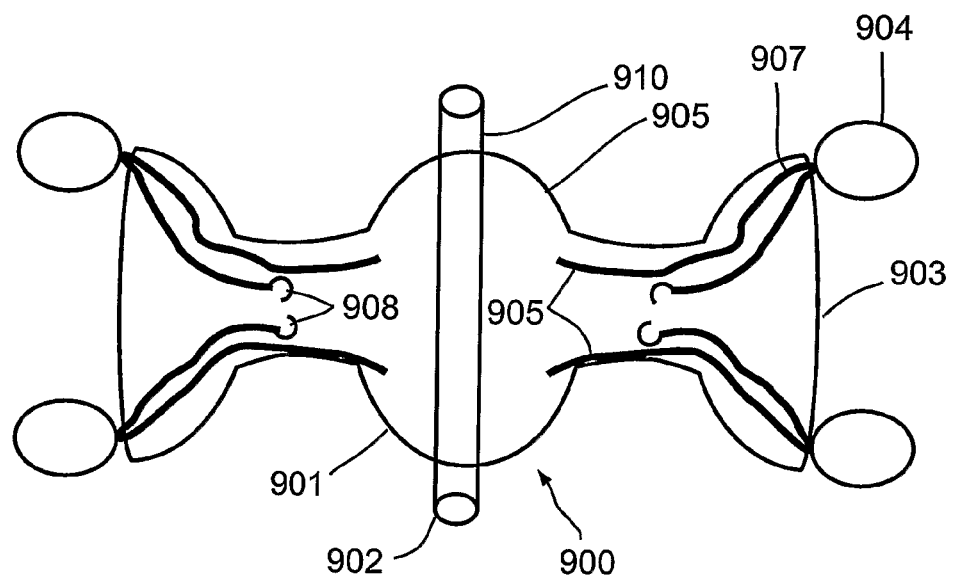
FIG. 9 is a schematic showing of a urethral support implant, in accordance with an exemplary embodiment of the invention.

FIG. 9 is a schematic showing of a urethral support implant 900, in accordance with an exemplary embodiment of the invention.

A particular feature of urethral support is that, in some embodiments, forces are applied to the support element only intermittently, for example, during sneezing.

Referring specifically to FIG. 9, device 900 comprises a tissue reinforcing means strip 901 such as a mesh that is placed under a urethra 902. Optionally, lateral ends 903 of the mesh are attached to one or more biodegradable inflatable balloons 904 (e.g., one or two on either side of the urethra), for example as described herein.

In an exemplary use, a small incision is performed over the urethra in the anterior vaginal wall and the anchoring balloons are introduced, inflated and sealed, first on one side and then on the other side laterally towards the lateral side of the pelvis and/or behind the pubic bone and/or towards the obteurabor fossa and/or muscle or membrane. Optionally, introduction is using a tunneling method as described with respect to FIG. 8. Once the balloons are inflated and in place, this anchors the supporting strip of material bellow the urethra, optionally using minimal tissue dissection.

Mesh strip 901 may be of uniform width or of different width along its length. For example, as shown, the mesh may have a complex shape including both convex and concave sections. Optionally, strip 901 is wider under the urethra to provide support, thinner on both sides and again wider at its lateral ends to permit attachment to the latter pelvic wall. In an exemplary embodiment of the invention, the anchoring balloons remain inflated for a few weeks to a few months until ingrowth of tissue fixes the reinforcing strip in place and then the biodegradable balloons may completely dissipate. Optionally, parts of the mesh are covered with a biodegradable or other coating, to prevent adhesions.

Mesh strip 901 may be of fixed length or may be of an adjustable length, optionally using a ratchet mechanism. In an exemplary embodiment of the invention, such a ratchet mechanism comprises one or more threads or filaments 905 that is attached to a central segment 906 of the strip, and which filament passed through one of lateral mesh segments 907 that is attached to am anchoring balloon. Optionally, the thread or filament is provided with hooks, discs and/or other projections 208, or other ratchet means that permits its slippage in only one direction of the filament through an opening in the lateral mesh segment. Optionally, a thickening in the thread resists being pulled through a hole or mesh of the reinforcing strip, but may be manually pulled. Optionally, such a thickening is cone shaped, to better facilitate movement in one direction over the other. Optionally or alternatively, a hook is provided on a near end of the thread, to attach the thread to the reinforcement strip after the thread is pulled. Optionally, the thread is biodegradable. In an exemplary embodiment of the invention, the strip under the urethra is properly tensioned by pulling on the thread or filament first on one side and then on the other side. Alternatively, such a ratchet mechanism may be provided between a filament connected to the lateral mesh segment and that passes trough an opening in the central mesh segment. Optionally or alternatively, the reinforcing element itself is pulled through an opening therein or through a ring that couples the balloons to the strip.

In general, it should be noted that once the anchoring balloons are in place, various manipulations of the reinforcement element can be applied, including changing a shape (e.g., using a ratchet or inflation) thereof and/or changing a layout by selectively shortening and lengthening threads that couple the strip to the anchoring balloons at different sides thereof.

It should be noted that in device 900, the balloons are optionally to the side of the reinforcing element, so they do not directly push or pull the mesh at tissue. Optionally, one or more such pull/push balloons are provided.

In an exemplary embodiment of the invention, a single lumen (not shown) connects the various balloons. Optionally or alternatively, the balloons are pre-inflated. Optionally or alternatively, the balloons are inflated using a syringe with a needle that is inserted into the balloon and that, once removed, allows the balloon to self seal.

Permanent Implant

In an exemplary embodiment of the invention, the permanent implant is a reinforcing element, optionally in the form of a mesh or fabric. Optionally, the mesh is manufactured of a biocompatible non-resorbable material such as but not limited to polypropylene, polyethylene, polyester, metal, ceramic, natural fibers, exoplants, and/or any combination thereof.

In some embodiments, the mesh also biodegardes/bioabsorbes, albeit slower than the expandable elements, for example, being made of PLA, PLGA, polycaprolactone and/or any combination thereof.

In an exemplary embodiment of the invention, the mesh is a flattened shape. In an exemplary embodiment of the invention, the ratio between maximum dimension and thickness of the mesh is greater than 3:1, 4:1, 7:1, 10:1 or intermediate values. In an exemplary embodiment of the invention, the mesh has a minimal dimension, of thickness of at most, 5 mm, 3 mm, 2 mm, 1 mm, or intermediate or smaller values.

In some embodiments, the mesh is a three dimensional shape, such as a spheroid or a cylinder, optionally supported form within by one or more bioabsorbable elements. For example, the mesh having a ratio between maximum dimensions in any three orthogonal axes of less than 3:1. Optionally or alternatively, the mesh has a minimal dimension of at least 2, 3, 4, 5, 6, 10 mm.

In an exemplary embodiment of the invention, the mesh is flexible, optionally elastic alternatively, pliable. For example, the mesh may be formed of fabric (e.g., woven, knit, felt).

In an exemplary embodiment of the invention, the mesh is planar, but other shapes may be provided as well, for example, cone shaped, ball shaped and cylinder shaped. Optionally or alternatively, the mesh is cast. Optionally or alternatively, the mesh is formed of a monofilament. Optionally or alternatively, the mesh is formed of metal, such as titanium or stainless steel. In an exemplary embodiment of the invention, the mesh is configured to not be expandable, to not be stretchable and/or to not have an elastic response.

Optionally or alternatively, to a mesh, other ingrowth/fibrosis enhancing designs may be provide, for example, a felt material, a pitted surface, and/or a surface with through holes formed thereon.

In an exemplary embodiment of the invention, the mesh is securely attached to the bioabsorbable implant, optionally fixed thereto, for example, using adhesive or being embedded in a material thereof. Alternatively, the attachment is looser, for example, using one or more sutures, tubes and/or being attached only at a small number of points thereto. Optionally, this allows some relative motion between the degrading and non-degrading parts of an implant and/or between expanding and non-expanding parts of the implant.

Bioabsorbable Implant

In an exemplary embodiment of the invention, the bioabsorbable implant portion is selected to have a working time sufficient for an expected tissue fibrosis time. Optionally, a plurality of different kits is provided and a physician can choose a kit with a desired working time.

In an exemplary embodiment of the invention, the expandable elements are inflatable balloons made of, for example, PLA, PLGA, polycaprolactone, polydiaxone, collagen, or any combination thereof.

In an exemplary embodiment of the invention, a balloon as described in US Patent Application published on 7 Feb. 2008 under Publication No. 2008-0033471-A1, is used, albeit possible of different size and/or shape.

In an exemplary embodiment of the invention, the expandable elements have a smooth surface and/or elute materials that discourage fibrosis and/or tissue ingrowth. Optionally, the balloons are seamless.

Optionally or alternatively, to balloons, the expandable elements may elastically expand or expand when absorbing fluid. For example, the expandable element may be solid and/or be in the form of a sponge. In an exemplary embodiment of the invention, an elastically expanding element is provided constrained by an over tube, such that when the element is released form the overtube, its diameter increased, for example, by a ratio of 2:1, 3:1 or more, as compared to the overtube diameter.

In an exemplary embodiment of the invention, the balloons are filed with gas, biocompatible solutions and/or with biocompatible biodegradable gels. Optionally, the injected material sets to a harder condition, before being bioabsorbed. The balloons may be provided with a sealing mechanism consisting of a means such as but not limited to plugs, valves, self sealing membranes, external compression rings and/or clips. Optionally or alternatively, a balloon is expanded by pushing into the balloon solids, optionally elastic, such as wires, soft silicon elements, threads and/or beads.

In an exemplary embodiment of the invention, the balloon is inflated with a pressure that allows the balloon to remain soft, for example as soft as surrounding tissue. For example, the balloon may be formed with consistency and/or softness and/or pliability of (or within 10% of) muscle, fascia, fat tissue and/or other tissue for which it is intended to be used with. In some cases, the balloons are made stiffer than surrounding tissues, for example, by 10%, 20%, 30%, 50% or more or intermediate numbers. In some cases, the implant is made softer than surrounding tissues. Optionally, mechanical properties similar to that of breast implants are provided.

The sizes of the balloons may be chosen according to the spaces into which these the devices are to be deployed. Various balloon shapes may be provided, for example, spheroids, ellipsoids, cylinders. In some cases, the balloon is selected to have a tissue matching contour (e.g., protrusions and/or depression) and/or to be flat, optionally to reduce a distraction force applied to nearby tissue. Optionally, ratios similar to those as described for a reinforcement element are used for defining volumetric shapes of balloons.

Tissue and Device Parameters

In an exemplary embodiment of the invention, the devices are used for soft tissue, which include, for example muscle, fat, fascia and subcutaneous tissues.

In an exemplary embodiment of the invention, the implant elutes various pharmaceuticals, for example, ingrowth and/or fibrosis enhancing or retarding materials, anti-inflammatories, anti-biotics and/or painkillers. Different parts of the device may elute different materials, often of opposing functionality, for example, pro and anti-adhesion materials.

Various sizes may be provided, depending on the application. For example a planar mesh may be, for example, of dimension of 20×20 mm, 303×30 mm, 50×50 mm or smaller greater or intermediate size. Rectangular shapes may be provided as well and so may be circular other shapes. A balloon (or other expanding elements) may be, for example, 1 mm in diameter, 3 mm in diameter, 5 mm in diameter, 10 mm in diameter, 20 mm in diameter, 50 mm in diameter or smaller, intermediate or greater diameters. Optionally, the balloon is elongate, for example, having a long axis of 10 mm, 20 mm, 30 mm, 50 mm or smaller or intermediate length. Optionally, the balloon is flattened, for example, having a thickness of 10 mm, 5 mm, 1 mm or smaller or intermediate thicknesses. Op a cord connecting implant parts is smaller in diameter than 5 mm, 3 mm, 2 mm 1 mm or intermediate in size. Optionally, a compressed diameter of an implant is 10 mm, 5 mm, 3 mm, 2 mm or smaller or intermediate diameters.

Figure 10:
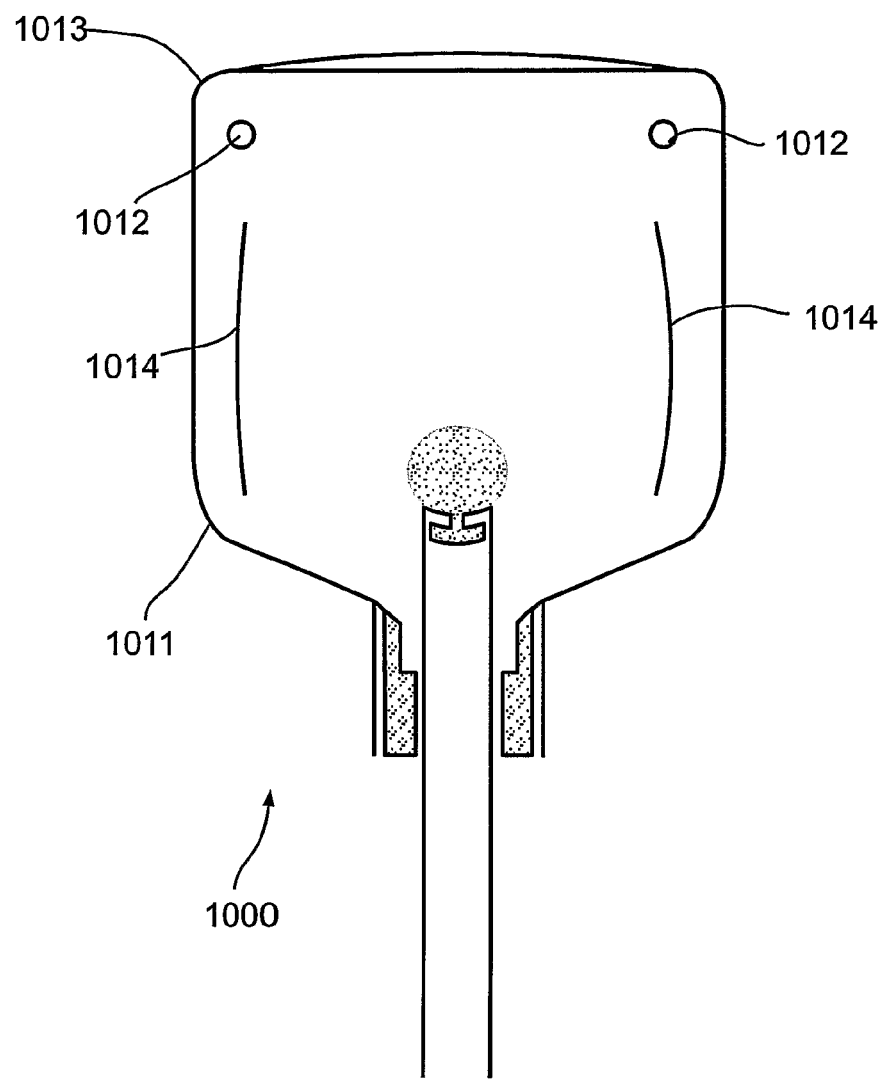
FIG. 10 is a schematic showing of an implant including radio-opaque markers, in accordance with an exemplary embodiment of the invention.

FIG. 10 is a schematic showing of a device implant 1000 including radio-opaque markers, in accordance with an exemplary embodiment of the invention. Whether using the device for tissue manipulation as described herein, or for other uses, such as surgical treatment, radiation treatment using ionizing radiation such as but not limited to: photon beam, thermal treatment such as thermal ablation or cryotherapy or chemical ablation, imaging of the device may be useful. In an exemplary embodiment of the invention, markers may be incorporated within the device (bioabsorbable portion and/or permanent portion), which markets may be detected by imaging means. Such markers may be for example radio-opaque markers such as metallic particles, rods, or wires that may be detected by imaging means such as radiography, fluoroscopy, and X-ray CT scanning. Such markers can indicate the proper position of the device, its orientation and/or its expansion in one or more planes. Other markers may be substances of high atomic weight such as barium, iodinated substances, gadolinium that may be incorporated diffusely or at particular regions in the device wall or within the inner space of the expanded device (e.g., provided with an inflation fluid). Other markers which may be used include hyper-echoic substances in case of using ultrasound, paramagnetic substances such as gadolinium in case of MRI, and radioactive isotopes in case of nuclear medicine imaging. Optionally, the markers are used to track the device and detect if it remains operative, for example, to see if the bioabsorbable anchoring failed and the reinforcing part moved.

FIG. 10 shows a device 1000 including a balloon 1011 with small particles 1012 incorporated into its walls 1013. Such particles may be, for example, elongated such as rods or be spherical. Optionally or alternatively, one or more wires 1014 may be incorporated into the wall of the device. Optionally or alternatively, such markers are incorporated into the reinforcing element, barbs and/or an inflation fluid.

Kits

In an exemplary embodiment of the invention, devices as described herein are provided as parts of kit, optionally with instructions, optionally in sterile form. Such a kit may include, for example, one or more devices, one or more delivery systems, an incision forming means and/or an inflation means.

General

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes, as relevant, one or more of abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating vaginal prolapse of a patient, the method comprising:
    a. providing a prosthesis comprising inflatable bioabsorbable implant and a permanent implant, wherein:
        i. the inflatable bioabsorbable implant is a seamless balloon comprising two flattened surfaces facing in opposite directions, configured to regulate tissue adhesion and to separate tissues by inflation; and
        ii. the permanent implant comprises a mesh and is attached to only a given one of the two flattened surfaces of the bioabsorbable implant so that only one of the two flattened surfaces faces the permanent implant, the permanent implant being adapted to cause a soft tissue reaction of adhesion to reinforce said adjacent tissue;
    b. positioning the permanent implant between the vaginal tissue and other tissue of the patient;
    c. inflating the bioabsorbable seamless balloon so that (i) during the inflation, the fluid enters into the seamless balloon via a tube that is parallel to the given one of the flattened surfaces; and (ii) the inflation drives separation of the vaginal tissue from the other tissue;
    d. sealing the inflated bioabsorbable and seamless balloon;
    e. allowing the inflated and sealed bioabsorbable balloon to biodegrade or bioabsorb after the permanent implant is fixed by fibrosis tissue.

2. The method of claim 1 wherein said flattened surfaces are flat when said inflatable bioabsorbable implant is inflated.

3. The method of claim 1 wherein the sealed and inflated bioabsorbable balloon is used to anchors the mesh in its place until the mesh sets to tissue.

4. The method of claim 3 wherein, in step (d), the inflated bioabsorbable and seamless balloon is sealed so that a pressure therewithin exceeds one atmosphere.

5. The method of claim 3 wherein the sealed and inflated bioabsorbable balloon remains inflated within the body for at least a few weeks.

6. The method of claim 3 wherein the sealed and inflated bioabsorbable balloon remains inflated within the body for few weeks to a few months.

7. The method of claim 1 wherein the sealed and inflated bioabsorbable balloon remains inflated within the body for at least a few weeks.

8. The method of claim 7 wherein, in step (d), the inflated bioabsorbable and seamless balloon is sealed so that a pressure therewithin exceeds one atmosphere.

9. The method of claim 1 wherein the sealed and inflated bioabsorbable balloon remains inflated within the body for few weeks to a few months until tissue ingrowth to the mesh occurs.

10. The method of claim 1 wherein, in step (d), the inflated bioabsorbable and seamless balloon is sealed so that a pressure therewithin exceeds one atmosphere.

11. The method of claim 10 wherein, in step (d), the inflated bioabsorbable and seamless balloon is sealed by a bioabsorbable plug.

12. The method of claim 1 wherein the balloon has only a single opening, and step (d) is performed by sealing the single opening of the balloon.

13. A method of treating vaginal prolapse of a patient, the method comprising:
   a. providing a prosthesis comprising inflatable bioabsorbable implant and a permanent implant, wherein:
      i. the inflatable bioabsorbable implant is a seamless balloon comprising two flattened surfaces facing in opposite directions, configured to regulate tissue adhesion and to separate tissues by inflation; and
      ii. the permanent implant comprises a mesh and is attached to only a given one of the two flattened surfaces of the bioabsorbable implant so that only one of the two flattened surfaces faces the permanent implant, the permanent implant being adapted to cause a soft tissue reaction of adhesion to reinforce said adjacent tissue;
   b. positioning the permanent implant between the vaginal tissue and other tissue of the patient;
   c. inflating the bioabsorbable seamless balloon so that (i) during the inflation, the fluid enters into the seamless balloon via a tube that is parallel to the given one of the flattened surfaces; and (ii) the inflation drives separation of the vaginal tissue from the other tissue;
   d. sealing the inflated bioabsorbable and seamless balloon;
   e. allowing the inflated and sealed bioabsorbable balloon to biodegrade or bioabsorb after the permanent implant is fixed by fibrosis tissue, wherein the inflated and sealed bioabsorbable balloon remains attached to the mesh to maintain a shape of the mesh until the mesh sets to tissue.

14. The method of claim 13 wherein said flattened surfaces are flat when said inflatable bioabsorbable implant is inflated.

15. The method of claim 13 wherein the sealed and inflated bioabsorbable balloon is used to anchor the mesh in its place until the mesh sets to tissue.

16. The method of claim 15 wherein, in step (d), the inflated bioabsorbable and seamless balloon is sealed so that a pressure therewithin exceeds one atmosphere.

17. The method of claim 15 wherein the sealed and inflated bioabsorbable balloon remains inflated within the body for few weeks to a few months.

18. The method of claim 13 wherein the sealed and inflated bioabsorbable balloon remains inflated within the body for few weeks to a few months until tissue ingrowth to the mesh.

19. The method of claim 18 wherein, in step (d), the inflated bioabsorbable and seamless balloon is sealed by a bioabsorbable plug.

20. The method of claim 13 wherein the balloon has only a single opening, and step (d) is performed by sealing the single opening of the balloon.

* * * * *